United States Patent
Hester et al.

(10) Patent No.: US 12,306,152 B2
(45) Date of Patent: May 20, 2025

(54) METHOD FOR TESTING A CHROMATOGRAPHY DEVICE USED FOR ION EXCHANGE

(71) Applicant: Solventum Intellectual Properties Company, Maplewood, MN (US)

(72) Inventors: Jonathan F. Hester, Hudson, WI (US); Eric J. Olson, Prior Lake, MN (US); Francis E. Porbeni, Woodbury, MN (US); Andrew W. Vail, Bayport, MN (US); Alexei M. Voloshin, Woodbury, MN (US)

(73) Assignee: Solventum Intellectual Properties Company, Maplewood, MN (US)

( * ) Notice: Subject to any disclaimer, the term of this patent is extended or adjusted under 35 U.S.C. 154(b) by 838 days.

(21) Appl. No.: 17/288,031

(22) PCT Filed: Dec. 16, 2019

(86) PCT No.: PCT/IB2019/060866
§ 371 (c)(1),
(2) Date: Apr. 23, 2021

(87) PCT Pub. No.: WO2020/128797
PCT Pub. Date: Jun. 25, 2020

(65) Prior Publication Data
US 2021/0396725 A1 Dec. 23, 2021

Related U.S. Application Data

(60) Provisional application No. 62/783,319, filed on Dec. 21, 2018.

(51) Int. Cl.
*G01N 30/96* (2006.01)
*C07K 1/22* (2006.01)
*G01N 30/88* (2006.01)

(52) U.S. Cl.
CPC .............. *G01N 30/96* (2013.01); *C07K 1/22* (2013.01); *G01N 2030/889* (2013.01)

(58) Field of Classification Search
CPC ..... G01N 30/96; G01N 2030/899; C07K 1/22
See application file for complete search history.

(56) References Cited

U.S. PATENT DOCUMENTS

| | | |
|---|---|---|
| 7,281,410 B2 | 10/2007 | Phillips |
| 7,732,216 B2 | 6/2010 | Nochumson |
| 8,328,023 B2 | 12/2012 | Weiss |
| 8,459,470 B2 | 6/2013 | Weiss |
| 8,551,894 B2 | 10/2013 | Seshadri |
| 8,586,338 B2 | 11/2013 | Etzel |
| 8,652,582 B2 | 2/2014 | Bothof |
| 8,846,203 B2 | 9/2014 | Bothof |

(Continued)

FOREIGN PATENT DOCUMENTS

| | | |
|---|---|---|
| WO | WO 2007-120272 | 10/2007 |
| WO | WO 2008-008872 | 1/2008 |

(Continued)

OTHER PUBLICATIONS

Gavara, "Preparation, characterization, and process performance of composite fibrous adsorbents as cation exchangers for high throughput and high capacity bioseparations", Journal of Chromatography B, 2012, vol. 903, pp. 14-22.

(Continued)

*Primary Examiner* — Jill A Warden
*Assistant Examiner* — Alex Ramirez

(57) ABSTRACT

Described herein is method for testing an ion exchange chromatography device. The method includes monitoring both a binding and a non-binding species and determining their breakthrough point to determine a net breakthrough value. The method can be used to determine the integrity of the chromatography device, ensure that the chromatography device possesses the expected adsorbent capacity, and/or determine viral clearance of the chromatography device.

17 Claims, 6 Drawing Sheets

— Chloride Breakthrough Curve
× Two points defining linear baseline (dashed line)
✕ Minimum value of electrode response
○ 1% breakthrough point

(56) References Cited

U.S. PATENT DOCUMENTS

| | | |
|---|---|---|
| 8,969,094 B2 | 3/2015 | Demmer |
| 9,272,246 B2 | 3/2016 | Rasmussen |
| 9,375,499 B2 | 6/2016 | Etzel |
| 9,434,829 B2 | 9/2016 | Rasmussen |
| 9,616,394 B2 | 4/2017 | Bothof |
| 9,650,470 B2 | 5/2017 | Bothof |
| 9,821,276 B2 | 11/2017 | Berrigan |
| 2008/0299672 A1* | 12/2008 | Nochumson ........... G01N 30/89 436/161 |
| 2012/0252091 A1 | 10/2012 | Rasmussen |
| 2012/0276652 A1* | 11/2012 | Demmer ................ G01N 30/88 436/163 |
| 2014/0301977 A1* | 10/2014 | Nadarajah ................ C07K 1/16 530/391.1 |
| 2018/0257042 A1 | 9/2018 | Hester |
| 2018/0356374 A1* | 12/2018 | Northrup ........... G01R 31/2896 |

FOREIGN PATENT DOCUMENTS

| | | |
|---|---|---|
| WO | WO 2009-148869 | 12/2009 |
| WO | WO 2011-082727 | 7/2011 |
| WO | WO 2013-096322 | 6/2013 |
| WO | WO 2017-069965 | 4/2017 |

OTHER PUBLICATIONS

Lendero, "; Simple method for determining the amount of ion-exchange groups on chromatographic supports", Journal of Chromatography A, 2005, vol. 1065, pp. 29-38.

Lendero, "Characterization of ion exchange stationary phases via pH transition profiles", Journal of Chromatography A, 2008, vol. 1185, pp. 59-70.

Plieva, Characterization of supermacroporous monolithic polyacrylamide based matrices designed for chromatography of bioparticles, Journal of Chromatography B 2004, vol. 807, pp. 129-137.

Podgornik, "Construction of Large-Volume Monolithic Columns", Analytical Chemistry, 2000, vol. 72, pp. 5693-5699.

Podgornik, "Noninvasive methods for characterization of large-volume monolithic chromatographic columns", Chemical Engineering & Technology, 2005, vol. 28, No. 11, pp. 1435-1441.

International Search Report for PCT International Application No. PCT/IB2019/060866, mailed on Apr. 3, 2020, 5 pages.

* cited by examiner

— Potassium Breakthrough Curve
× Two points defining linear baseline (dashed line)
∗ Maximum value of electrode response
○ 1% breakthrough point

METHOD FOR TESTING A CHROMATOGRAPHY DEVICE USED FOR ION EXCHANGE

TECHNICAL FIELD

A method for testing an ion exchange chromatography device is discussed. Such a method can be used to determine the integrity of the chromatography device, ensure that the chromatography device possesses the expected adsorbent capacity, and/or predict whether the chromatography device is capable of achieving an expected level of viral clearance in a subsequent flow-through operation.

SUMMARY

There is a desire to identify a method that can be conducted prior to use to determine the integrity of a chromatography device, ensure that the chromatography device possesses the expected adsorbent capacity, and/or predict whether the chromatography device is capable of achieving an expected level of viral clearance in a subsequent flow-through operation.

In one aspect, a method for testing a chromatography device is discussed, wherein the chromatography device has an inlet and an outlet and contains an ion exchange media, the method comprising:

providing the ion exchange media having a first ion bound to the ion exchange sites of the ion exchange media;

contacting the ion exchange media with a challenge solution, wherein the challenge solution comprises (i) a second ion, which binds to the ion exchange media and (ii) a non-binding species, which does not bind to the ion exchange media, wherein the second ion has a higher binding affinity to the ion exchange media than the first ion;

monitoring an outlet fluid from the outlet of the chromatography device with at least one detector wherein both the second ion and the non-binding species are monitored;

recording a breakthrough value of (i) the second ion and (ii) the non-binding species; and calculating a net breakthrough value using the breakthrough value of the non-binding species and the breakthrough value of the second ion.

In one embodiment, the method as disclosed herein is used to determine integrity of the chromatography device.

In another embodiment, the method as disclosed herein is used to determine the adsorbent capacity of the chromatography device.

In yet another embodiment, the method as disclosed herein is used to predict whether the chromatography device is capable of achieving an expected level of viral clearance in a subsequent flow-through operation.

The above summary is not intended to describe each embodiment. The details of one or more embodiments of the invention are also set forth in the description below. Other features, objects, and advantages will be apparent from the description and from the claims.

DETAILED DESCRIPTION

As used herein, the term

Figure 1:
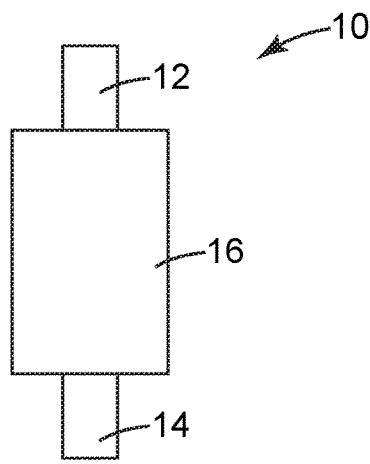
FIG. 1 is a schematic drawing of a chromatography device comprising an inlet, an outlet, and chromatography media.

"a", "an", and "the" are used interchangeably and mean one or more; and

"and/or" is used to indicate one or both stated cases may occur, for example A and/or B includes, (A and B) and (A or B).

Also herein, recitation of ranges by endpoints includes all numbers subsumed within that range (e.g., 1 to 10 includes 1.4, 1.9, 2.33, 5.75, 9.98, etc.).

Also herein, recitation of "at least one" includes all numbers of one and greater (e.g., at least 2, at least 4, at least 6, at least 8, at least 10, at least 25, at least 50, at least 100, etc.).

As used herein, "comprises at least one of" A, B, and C refers to element A by itself, element B by itself, element C by itself, A and B, A and C, B and C, and a combination of all three.

Manufacturing of commercial quantities of therapeutically useful targeted biomaterials, such as proteins, can be accomplished by growing cells or organisms that are engineered to produce a desired biological product in bioreactors under controlled conditions. The technology usually involves, for example, the fermentation of microorganisms which have been altered through recombinant DNA techniques or the culturing of mammalian cells, insect cells, yeast cells, or other living organisms which have been altered through recombinant DNA techniques. The cells or organisms are suspended in a broth which contains the salts, sugars, proteins, and various factors necessary to support the growth of particular cells or organisms. The desired product may be either secreted by the cells or organisms into the broth or retained within the cell or organism body. The harvested broth is then processed to isolate, purify, and concentrate the desired product.

Ion exchange chromatography is one technique that can be used to isolate and/or purify the targeted biomaterial. Ion exchange chromatography may be performed using anionic (e.g., strong or weak acid) or cationic (e.g., strong or weak base) ion exchange resins, beads, or other porous or non-porous media comprising ion exchange functional chemistry, such as chromatography monoliths, chromatography membranes, or functional nonwovens, herein referred to as chromatography media. These chromatography media can be arranged in packed columns, in monolith devices, or in filter devices, for example, which are herein referred to as chromatography devices.

Before running the broth through the chromatography device, it is advantageous to ensure that the chromatography device is integral, meaning that the chromatography device does not contain any leaks or defects in construction that might enable the fluid containing the targeted biomaterial to bypass any portion of the chromatography media contained within the device. It can also be advantageous to validate that the chromatography device has at least a minimum expected ion exchange capacity (e.g., that it does not contain a deficient quantity of ion exchange functional media). Finally, it can be advantageous to validate that the chromatography device can provide, in a subsequent flow-through operation, the viral reduction expected of an integral device with the expected ion exchange capacity. A procedure to make any one or more of the above determinations prior to processing the product-containing fluid may be referred to as a "pre-use integrity test."

In many cases, a pre-use integrity test is preferable to a "post-use" integrity test, wherein the assessment of whether the chromatography device is integral is performed after processing the product-containing fluid using the chromatography device. This is because a pre-use integrity test reduces the risk of processing a valuable product-containing fluid using a deficient chromatography device. A post-use integrity test may result in discovery of a deficiency in the chromatography device only after it has been used to process the product-containing fluid. This might result, at best, in a need to re-process the product-containing fluid using another chromatography device or, at worst, a need to dispose of the valuable product-containing fluid. To be useful as a pre-use integrity test, any method of determining the integrity, ion exchange capacity, and/or expected viral clearance capability of a chromatography device must be non-destructive. That is, the performance of the pre-use integrity test must not affect the subsequent performance of the chromatography device in achieving the desired separation of constituents within the product-containing fluid.

One commonly used type of integrity test for membrane filter devices, including chromatography membrane devices, is a pressure hold or pressure decay integrity test. As described, for example, in ASTM Standard D6908, this type of test involves, first, filling the chromatography device with a wetting fluid. The upstream side of the device is then pressurized with a gas, such as air, at a pressure at which the wetting fluid is displaced from the upstream headspace of the device but remains held within the pores of the chromatography media by capillary forces. Measurement of either an excessively fast pressure decay or an excessively high gas flow downstream of the chromatography device indicates leakage of gas through a hole in the media or a faulty seal. A similar type of test is a bubble point test, as described in ASTM Standard F316. In this type of test, the chromatography device is filled with a wetting fluid, after which a gas pressure is applied to the upstream side of the device. The upstream gas pressure is gradually increased while the flow of gas at the downstream side of the device is monitored. Initially, the wetting fluid is retained within the media by capillary forces and the downstream gas flow is very low. Once the upstream gas pressure reaches the bubble point pressure of the media, the largest pores in the media are cleared of wetting fluid and the downstream gas flow rapidly increases. Observation of an increase in downstream gas flow at an applied upstream pressure less than the expected bubble point pressure of the media indicates a hole or a defective seal in the chromatography device.

Due to the potential to negatively affect the subsequent performance of the chromatography device when processing the product-containing fluid, the above described gas pressure-based tests may not be useful as a pre-use integrity test. In chromatography devices containing multiple layers of ion exchange functional media, for example, the gas pressure-based tests can result in the introduction of air pockets between partially wetted media layers. These air pockets may be difficult to remove, resulting in poor utilization of the chromatography media during subsequent processing of the product-containing fluid. Additionally, while these gas pressure-based integrity test procedures are useful for detecting mechanical defects in chromatography devices, such as holes or faulty seals, they are not capable of detecting other deficiencies which might result in substantially reduced separation performance, including a reduced capability of removing viruses. For example, a membrane chromatography device containing an ion exchange functional membrane having the expected pore size distribution, but having a region not functionalized with the ion exchange chemistry, would pass the gas pressure-based integrity test, but may fail to remove any viruses wherein the viral reduction relies on substantially uniform chemical functionality across the membrane area. Additionally, gas pressure-based integrity tests are generally not useful for resin or bead-based chromatography devices.

A procedure for determining the integrity, ion exchange capacity, and/or expected viral clearance capability of a chromatography device would advantageously have the following features. The procedure would be non-destructive so as to be useful as a pre-use integrity test. The procedure would be capable of detecting, in addition to mechanical defects in the chromatography device, deficiencies in the functional media itself (e.g., insufficient ion exchange capacity) that would result in reduced bioseparation performance, including reduced reduction of protein contaminants or reduced viral reduction performance. The procedure would be suitable for use in a commercial manufacturing environment, utilizing non-hazardous, inexpensive, and commonly available reagents and requiring non-hazardous steps (e.g., not requiring extremes in pH, temperature, etc. that might pose hazards to operators). In some embodiments, the procedure may be predictive of the viral clearance capability of the chromatography device. As some chromatography devices have very low permeability for water of such low conductivity (for example, chromatography devices comprising ion exchange functional nonwoven media as described in U.S. Pat. No. 9,821,276), in some embodiments, the procedure would involve no flow of substantially pure water (or water having a conductivity less than about 3 mS/cm) through the chromatography device.

In the present disclosure, a novel method of testing ion exchange chromatography devices is described. Such testing can be used to determine a net breakthrough value, which can be compared to a reference breakthrough value to evaluate the integrity, confirm the adsorbent capacity, and/or predict the viral clearance performance of the chromatography device in a subsequent flow-through operation. Embodiments of the presently disclosed method have many or all of the advantageous features listed above.

The method disclosed herein is useful in the testing of chromatography devices. FIG. 1 shows chromatography device 10 comprising inlet 12 and outlet 14 and chromatography media housed in vessel 16 therebetween, wherein inlet 12 and outlet 14 are fluidly connected. The chromatography media comprises an ion exchange media, which may be anionic (strong or weak) or cationic (strong or weak) in nature. The chromatography device may comprise additional separation media, including, but not limited to, a different ion exchange media, particle size filters, and chromatography media that separates analytes based on interactions other than ion exchange, such as hydrophobic interaction, affinity, etc. The chromatography media can refer to chromatography membranes, chromatography monoliths, chromatography resins or beads, or other porous or nonporous media comprising ion exchange functional chemistry, such as functional nonwoven materials as described in U.S. Pat. No. 9,821,276 (Berrigan, et al.), herein incorporated by reference.

Described below is the test method. The method is directed toward ion exchange chromatography with the understanding that the solutions disclosed below are made to enter the chromatography device via the inlet as feed, pass through the chromatography media (including the ion exchange media), and then exit the chromatography device via the outlet (the solution exiting the outlet herein is referred to as eluate).

The test method involves a challenge step during which a challenge solution is passed through the chromatography device from the inlet to the outlet so as to contact the ion exchange media. During the challenge, a net breakthrough value is measured. The net breakthrough value is then compared with the net breakthrough value of a reference (e.g., an integral chromatography device having substantially the intended ion exchange capacity) to assess the integrity, ion exchange capacity, and/or expected viral clearance performance of the tested chromatography device.

Prior to conducting the challenge, substantially all of the active ion exchange sites on the ion exchange media should be bound with a first ion. For example, if the ion exchange media is an anion exchange media, meaning it binds anions, the first ion is an anion. Alternatively, if the ion exchange resin is a cation exchange resin, meaning it binds cations, the first ion would be a cation. Substantially all means that at least about 90, 95, or even 98% of the active ion exchange sites within the ion exchange media are bound with the first ion.

In some embodiments, the first ion is bound to substantially all of the ion exchange sites of the ion exchange media as a result of the media manufacturing process. For example, the chromatography device is commercially available with the desired first ion already bound to the ion exchange media.

In other embodiments, the as-manufactured media might be bound with a different counter-ion or a mixture of counter-ions. In these embodiments, prior to running the aforementioned challenge, one or more flow-through steps may be conducted to ensure that substantially all of the ion exchange sites on the ion exchange media are bound with the first ion. Prior to the challenge, a first solution is passed through the chromatography device, from the inlet to the outlet, so as to contact the ion exchange media. Even in cases in which the chromatography device is commercially available with the desired first ion already bound to the ion exchange media, it may sometimes be desirable to flush the chromatography device with a first solution, for example, to remove all air from the device and/or to remove additives such as humectants that may be present in the media within the device.

When using a first solution, the first solution could be, for example, an aqueous buffer comprising the first ion or an aqueous salt solution comprising the first ion as a constituent. A sufficient amount of the first solution is contacted with the ion exchange resin such that substantially all of the ionic sites on the ion exchange media are bound with the first ion. The active ion exchange sites may be bound with the first ion, by flowing a concentrated solution of first ions through the chromatography device for a given time. In one embodiment, a bolus of a highly concentrated solution of the first ion is used to bind the active sites of the ion exchange media, which can advantageously reduce the run time of the test method and the volume of the first solution required. Exemplary concentrations of the first ion in the first solution are at least 0.1, 0.5, 1, or even 2 molar, and at most 10, or even 15 molar, or even up to the solubility limit of the salt comprising the first ion.

When substantially all of the ion exchange sites on the ion exchange media are bound with the first ion, the aforementioned challenge step is performed as follows. A challenge solution comprising a second ion and a non-binding species is passed through the chromatography device, from the inlet to the outlet, such that the challenge solution contacts the ion exchange media. The second ion binds to the ion exchange resin, displacing, or exchanging with, the first ion, which re-enters the solution. As with the first ion, if the ion exchange resin is an anion exchange resin, the second ion would be an anion. Alternatively, if the ion exchange resin is a cation exchange resin, the second ion would be a cation.

As is well known in the art, the affinity of an ion exchange resin to bind a particular ion is defined by a selectivity coefficient, which can be calculated by the measured ratios of ions in solution to ions bound to the ion exchange media at equilibrium. The higher the selectivity coefficient for a particular ion, the higher the affinity or preference of the resin to bind that ion. Relative affinity values for ions are often calculated as follows. The relative affinity value of an ion exchange media for a reference ion is set to 1. The relative affinity value for another ion is then calculated by dividing its selectivity coefficient by the selectivity coefficient of the reference ion. Thus, a series of relative affinity values may be established, wherein the higher the relative affinity value of an ion is with respect to an ion exchange media, the greater the affinity of the media for binding that ion.

According to the method disclosed herein, the relative affinity value of the second ion is greater than the relative affinity of the first ion. In one embodiment, the method disclosed herein is very sensitive to small defects in the device and/or small differences in the ion exchange capacity of the media.

The non-binding species in the second solution is a species that is not retained by the ion exchange resin such that it traverses through the chromatography device with minimal to no interaction and at substantially the same rate as water. When the ion exchange media is an anion exchange resin, the non-binding species is selected from a cation or a neutral compound. When the ion exchange media is a cation exchange resin, the non-binding species is selected from an anion or a neutral compound. The concentration of the non-binding species in the second solution should be high enough such that it can be adequately detected by the detector. In one embodiment, the concentration of the non-binding species in the second solution is at least 1, 2, 4, or even 10 mM and at most 50, 75, or even 100 mM.

It is necessary that the non-binding species be substantially absent within the chromatography device prior to introduction of the challenge solution. For embodiments in which the ion exchange media is manufactured such that its binding sites are bound by the first ion, the manufacturing process must additionally provide that the ion exchange media and chromatography device are substantially free of the non-binding species (i.e., less than 1 mM with respect to the solution volume within a solution-filled device). Alternatively, the chromatography device must be flushed with a sufficient amount of fluid substantially free of the non-bonding species to result in its substantial removal from the chromatography device. For embodiments in which the first ion is bound to the ion exchange media by flushing the chromatography device with a first solution prior to the challenge test, the non-binding species must be substantially absent in the first solution. Immediately prior to conducting the challenge test, the nonbinding species should be present within the chromatography device at a concentration no more than 1 mM with respect to the solution volume within a solution-filled device.

In one embodiment, an optional dilute solution (or wash solution) can be used to wash the chromatography device after contact with the first solution. The dilute solution is substantially free of the second ion and the non-binding species, meaning that the dilute solution comprises less than 1 mM of each of the second ion and the non-binding species. In one embodiment, the dilute solution is water. In another embodiment, the dilute solution is a dilute salt solution. In another embodiment, the dilute solution is a dilute buffer solution. In one embodiment, the dilute solution comprises the first ion at a concentration lower than its concentration in the first solution. In one embodiment, the dilute solution comprises at least 1, 2, 5, or even 10 mM and at most 50, 75, or even 100 mM of the first ion.

The testing conditions, such as the flow rates, concentrations, temperatures and pressures, can be determined and carried out as is known by one of ordinary skill in the art. Typically, the test method is run at ambient temperature and pressure. In one embodiment, the flow rate is at least 0.5 milliliters per milliliter of ion exchange media volume per minute and at most 60 milliliters per milliliter of ion exchange media volume per minute. However, the flow rates may be adjusted based on the size of the chromatography device, the response time of the detector, and/or the concentrations of the solutions used.

The first and second ions are selected such that they selectively bind or adsorb to the ion exchange media, are selectively desorbed and eluted from the chromatography device, and the second ion needs to be adequately detected by the detector. A variety of first and second ions can be suitable for testing the ion exchange media. Preferably, the first and second ions are essentially non-toxic and non-hazardous.

Exemplary analyte packages for anion exchange chromatography devices are listed in Table 1. One set of embodiments includes an acetate first ion, a chloride second ion, and a potassium ion as the non-binding species. Another set of advantageous embodiments include iodide as the second ion. The analyte packages listed in Table 1 are not exhaustive and, having considered the packages listed, one of ordinary skill in the art would be able to apply the same principles to selecting other analyte packages by choosing anions for the first ion and second ion, wherein the second ion has a higher relative affinity value than the first ion, and a cationic or neutral species that is used for the non-binding species.

Exemplary analyte packages for cation exchange chromatography devices are listed in Table 2. An advantageous set of embodiments includes a lithium ion as the first ion. This set of embodiments is advantageous in many cases because lithium, having a low relative affinity value with respect to cation exchange media, is easily displaced during the challenge test by a variety of second ion types. Another advantageous set of embodiments includes a calcium ion as the second ion. These embodiments are advantageous in many cases because ion selective electrodes adapted for calcium are readily available and calcium, having a relatively high relative affinity value for cation exchange resins, easily displaces a variety of first ion types. The analyte packages listed in Table 2 are not exhaustive and, having considered the packages listed, one of ordinary skill in the art would be able to apply the same principles to selecting other analyte packages by choosing cations for the first ion and second ion, wherein the second ion has a higher relative affinity value than the first ion, and anionic or neutral species for the non-binding species.

In some embodiments, such as those listed in Tables 1 and 2, the non-binding species is an ion. In other embodiments, the non-binding species is a compound detectable by ultraviolet (UV) or visible radiation absorption, such as a compound comprising a chromophore or a dye. It is necessary that the non-binding compound have a net charge that is either neutral or the same charge as that of the ion exchange media. During the challenge test, the challenge solution is conveyed to the inlet of the chromatography device from a storage vessel, by means of a pump positioned between the storage vessel and the inlet of the chromatography device, through a conduit, like a pipe or flexible tubing, fluidly connecting the storage vessel and the chromatography device inlet. In some cases, the pump may be positioned downstream of the chromatography device outlet, providing a partial vacuum on the downstream side of the chromatography device and thus causing the challenge fluid to flow from the storage vessel to the chromatography device inlet. In still other cases, no pump may be used, but a positive pressure applied within the storage vessel causes the challenge fluid to flow through the conduit to the chromatography device inlet.

The challenge solution is passed through the chromatography device and the second ion displaces the first ion bound on the ion exchange media. The change in the concentration of the second ion in the eluate over a period of time is measured downstream of the chromatography device to provide a breakthrough curve for the second ion. Simultaneously, the change in the concentration of the non-binding species in the eluate over a period of time is measured downstream of the chromatography device, to provide a breakthrough curve for the non-binding species.

The eluate is monitored downstream of the outlet with at least one detector. The detector is selected such that the detector has the ability to monitor the analyte of interest (i.e., the second ion and/or the non-binding species). In the present disclosure, both the second ion and the non-binding species are monitored. Exemplary detectors include ultraviolet, conductivity, mass spectrometry, fluorescence, luminescence, and ion selective electrodes. In one embodiment, at least two detectors are used. In one embodiment, at least one detector is selective for a specific analyte, meaning that the detector can selectively detect the analyte of interest. Preferably, if two detectors are used, they are each positioned at the same distance downstream of the chromatography device outlet. If the detectors cannot be positioned at the same downstream position (for example, due to geometric constraints), the method can still be used so long as the volume of fluid separating the two detectors is known, or so long as the volume separating the two detectors is small relative to the volume inside the chromatography device (for example, less than about 5% of the chromatography device volume).

In one embodiment, at least one detector is an ion selective electrode. Ion selective electrodes may be used to selectively measure the concentration of substantially one particular ion such as sodium, potassium, calcium, chloride, iodide, or nitrate, for example. Suitable ion selective electrodes include, but are not limited to, combination ion selective electrodes available from Thermo Scientific under the following trade designations, such as THERMO SCIENTIFIC ORION Sure-Flow Fluoride Ion Selective Electrode (Item No. 9609BNWP), THERMO SCIENTIFIC ORION Sure-Flow Chloride Ion Selective Electrode (Item No. 9617BNWP), THERMO SCIENTIFIC ORION Sure-Flow Bromide Ion Selective Electrode (Item No. 9635BNWP), THERMO SCIENTIFIC ORION Sure-Flow Iodide Ion Selective Electrode (Item No. 9653BNWP), THERMO SCIENTIFIC ORION Sure-Flow Nitrate Ion Selective Electrode (Item No. 9307BNWP), THERMO SCIENTIFIC ORION Sure-Flow Sodium Ion Selective Electrode (Item No. 8611BNWP), THERMO SCIENTIFIC ORION Sure-Flow Potassium Ion Selective Electrode (Item No. 9719BNWP), THERMO SCIENTIFIC ORION Sure-Flow Cupric Ion Selective Electrode (Item No. 9629BNWP), THERMO SCIENTIFIC ORION Sure-Flow Cadmium Ion Selective Electrode (Item No. 9648BNWP), THERMO SCIENTIFIC ORION Sure-Flow Calcium Ion Selective Electrode (Item No. 9720BNWP), THERMO SCIENTIFIC ORION Sure-Flow Silver Ion Selective Electrode (Item No. 9616BNWP), and THERMO SCIENTIFIC ORION Sure-Flow Lead Ion Selective Electrode (Item No. 9682BNWP).

In one embodiment, at least one detector is a UV (ultraviolet) or UV-Vis (ultraviolet-visible) detector. UV or UV-Vis detectors are widely used on biopharmaceutical process control and analysis equipment, and can detect compounds that absorb UV radiation, such as compounds comprising chromophores or dyes. For example, suitable dyes include anionic dyes such as methyl orange, ethyl orange, acid red, and metanil yellow; as well as cationic dyes such as methylene blue and rhodamine B. Many other compounds are available that absorb in UV or visible wavelengths and could be useful, particularly as the non-binding species. Changes in the concentrations of compounds not comprising chromophores, including even simple ions, can also result in measurable UV or UV-Vis absorption changes. For example, it has been found that an increasing UV absorption signal at 280 nm is observed upon breakthrough of chloride ions through an anion exchange chromatography device previously equilibrated with acetate ions. Without wishing to be constrained by any particular physical theory, it is thought that this change in UV absorbance results from changes in the Raman scattering of water as the solution molality changes, resulting in changes in the incidence on the detector of radiation at 280 nm from a broadband radiation source. In any case, this observation renders UV absorption at 280 nm a useful detection means for the method of this disclosure when the first ion is acetate and either the second ion or the non-binding species is chloride.

Since ions are electrically conductive, in one embodiment, at least one detector is a conductivity detector.

Detection methods like UV absorption and conductivity may not be as selective and sensitive to the first ion, second ion, and non-binding species as ion selective electrodes. Thus, in some embodiments, ion selective electrodes may be used to detect one or more of these analytes, simultaneously with one or more other detection methods, while conducting a challenge test on a reference chromatography device. If it is observed that a change in the signal from an ion selective electrode coincides with a change in the signal from one of the less selective detection methods, the less selective detection method can then be used during future tests of the same type of chromatography device in the absence of the ion selective electrode.

Less frequently, mass spectrometry, fluorescence and/or luminescence can be used as a detector. These detection techniques can be very selective, but tend to be complicated and/or expensive to implement. Exemplary species that fluoresce include cations such as quinine and fluorescein; and anions such as sulfonated stilbenes, and rhodamine. Exemplary species that luminesce include luminol and bacterial luciferin.

The concentration profile for the non-binding species and the second ion are used to determine the breakthrough value for the non-binding species and the second ion, respectively. Breakthrough refers to the amount of time it takes the analyte of interest (e.g., the second ion or the non-binding species) to reach the detector. Breakthrough is observed by a change (either increase or decrease) in the detector signal over time. The time of breakthrough can be determined using a variety of techniques, as long as the determination is consistent.

Figure 2A:
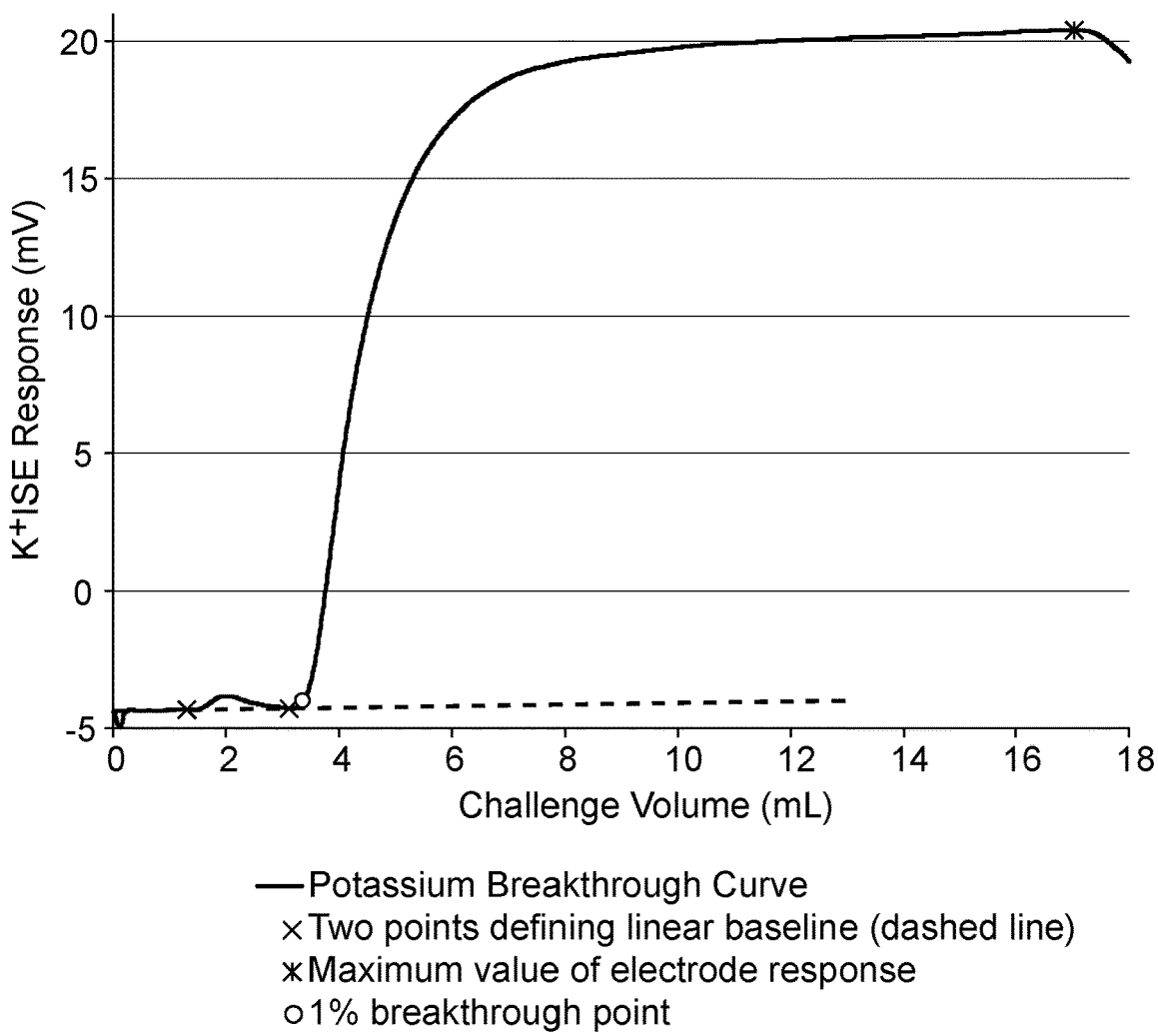
FIG. 2A is an example chromatogram illustrating an exemplary method for determining a breakthrough value for an analyte for which the detector response increases with increasing concentration of the analyte.

A technique for determining a breakthrough value according to one embodiment is illustrated in FIG. 2A, where the breakthrough of an analyte, potassium ions, is detected by a potassium ion selective electrode (ISE). Breakthrough of potassium ions results in an inflection followed by a steady increase in the measured electrode voltage. Two points are selected, denoted with "X" symbols in FIG. 2A, which define a baseline, shown as a dashed line in FIG. 2A, which forms a tangent with the portion of the chromatogram prior to breakthrough. The maximum value of the electrode response, denoted with an asterisk symbol in FIG. 2A, is identified. This maximum response value is associated with substantially complete breakthrough of potassium ions, such that the potassium ion concentration downstream of the chromatography device is roughly equal to that in the feed solution. The breakthrough value, denoted with a circle symbol in FIG. 2A, is then defined as the position on the x-axis at which the electrode response in the chromatogram rises above the defined baseline by a quantity equal to a selected percentage of the distance between the baseline and the maximum value of the electrode response. In the example shown in FIG. 2A, the selected percentage is 1% and the breakthrough value is determined to be 3.4 mL.

Figure 2B:
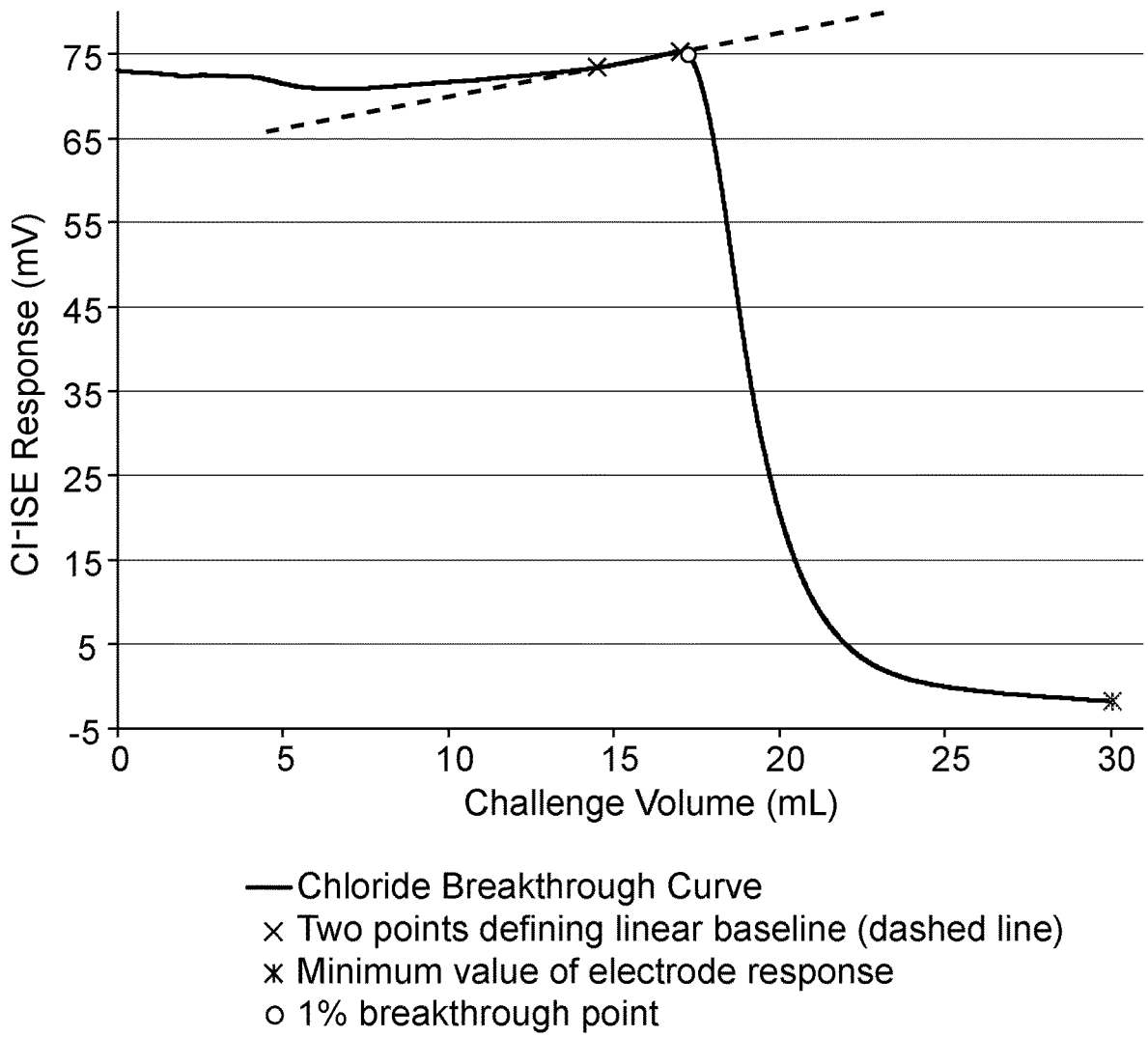
FIG. 2B is an example chromatogram illustrating an exemplary method for determining a breakthrough value for an analyte for which the detector response decreases with increasing concentration of the analyte.

FIG. 2B illustrates an analogous technique for determining the breakthrough value for a case in which the detector response decreases with increasing concentration of the analyte. In FIG. 2B, breakthrough of chloride ions is detected by a chloride ion selective electrode, and results in an inflection followed by a steady decrease in the measured electrode voltage. Two points are selected, denoted with "X" symbols in FIG. 2B, which define a baseline, shown as a dashed line in FIG. 2B, which forms a tangent with the portion of the chromatogram prior to breakthrough. The minimum value of the electrode response, denoted with an asterisk symbol in FIG. 2B, is identified. This minimum response value is associated with substantially complete breakthrough of chloride ions, such that the chloride ion concentration downstream of the chromatography device is roughly equal to that in the feed solution. The breakthrough value, denoted with a circle symbol in FIG. 2B, is then defined as the position on the x-axis at which the electrode response in the chromatogram declines below the defined baseline by a quantity equal to a selected percentage of the distance between the baseline and the minimum value of the electrode response. In the example shown in FIG. 2B, the selected percentage is 1% and the breakthrough value is determined to be 17.3 mL.

In one embodiment, a saturation signal for a detector is first established by exposing the detector directly to the challenge solution and recording the detector reading at that condition. Subsequently, a challenge test is conducted on a chromatography device, and breakthrough of an analyte is determined by extending a baseline taken at an early portion of the breakthrough curve for the analyte, prior to its breakthrough, and then recording the time or volume at which the detector signal changes a fixed percentage, for example, 0.1%, 0.5%, 1%, or 10% of the difference between the baseline value and the saturation value. This method is very similar to that depicted in FIGS. 2A and 2B, except that the prior establishment of a saturation signal for the detector enables determination of the breakthrough value without the necessity of collecting data for the entire chromatogram after breakthrough to identify its maximum or minimum value as depicted in those figures. That is, the challenge test can be stopped shortly after observing the inflection in the chromatogram associated with breakthrough of the analyte. In another embodiment, the derivative of the chromatogram is taken and the breakthrough time is determined by the maxima (or minima). By knowing the time that the breakthrough occurred and the flow rate, the breakthrough volume can be determined. The breakthrough value for an analyte may be a time, volume, mass, or other parameter associated with the quantity of the challenge solution that has passed through the chromatography device at the identified breakthrough point. In one embodiment, a selective detector (such as ion selective electrodes) could be used initially to develop the testing protocol, and after familiarity with the elution profile, a UV or conductivity detector could replace the ion selective electrodes.

After determining the breakthrough value of the non-binding species and the breakthrough value of the second ion, the net breakthrough value can be calculated. In one embodiment, the net breakthrough value is calculated by subtracting the breakthrough value of the non-binding species from the breakthrough value of the second ion. For example, the net breakthrough value for the example illustrated in FIGS. 2A and 2B, where potassium ions are the non-binding species and chloride is the second ion, is 17.3 mL minus 3.4 mL, or 13.9 mL.

Hold up volume (or dead volume or void volume) in liquid chromatography is the volume taken up by the solution and includes the tubing volume from the injector site to the chromatography media, any open spaces within the chromatography media and the vessel housing the chromatography media, and the tubing volume from the end of the chromatography media to the detector. In the case of the non-binding species, as the non-binding species is not retained by the ion exchange media, its breakthrough curve can be used to determine the hold up volume of the chromatography device and tubing. Since the hold up volume of the chromatography device is accounted for in the net breakthrough value, the net breakthrough value can be compared to a reference breakthrough value of known type and integrity to determine whether or not the chromatography device of the present method has integrity. For example, the same test method is run on a chromatography device of known type and integrity and the second ion and the non-binding species are monitored to determine the breakthrough values for the second ion and the non-binding species and this provides the reference. In some embodiments, the reference breakthrough curves, or reference breakthrough values, or reference net breakthrough value is provided by the manufacturer and/or supplier of the ion exchange media or chromatography device. For example, the reference breakthrough curves or net reference value(s) can be provided as an insert and/or as part of the instructions supplied with the ion exchange media or chromatography device. Since the void volume of the system is determined as part of the challenge test, the reference breakthrough values, net breakthrough value, or breakthrough curves can be compared to that of a test device, even if the test device is challenged on different equipment with a different void volume.

In one embodiment, the net breakthrough value of a chromatography device can be compared to the reference net breakthrough value to evaluate the integrity of the chromatography device. For example, the breakthrough value should be at least 85, 90, 92, or even 95% of the reference breakthrough value, when the chromatography device is run under a set of standard conditions (such as a set flow rate and temperature).

In one embodiment, the method disclosed herein can be utilized to determine breaches of the integrity of the chromatograph device, and thus, the user can determine that the chromatography device is defective and likely unfit for its intended purpose. There may be situations where, if the results show the breach of integrity is minor, the user may determine the breach has little or no effect on the device's performance. Thus, the user may determine that the performance of the device is acceptable.

The method as disclosed above may be used in a variety of chromatography media including one or more membranes or monoliths (e.g., polymerized gels, silica columns, ceramics, graphitized carbon), including commercially available membranes and monoliths. In some embodiments, the chromatography device, i.e., comprising the housing and the chromatography media sealed therein, is a preassembled device, e.g., wherein the media are sealed in the housing by the device manufacturer. In some other embodiments, the media are sealed in the housing by the end user. The chromatography devices can be suitable for treating a variety of fluids, e.g., to purify and/or concentrate one or more desired materials present in the fluids. For example, as mentioned above, the chromatography devices can be suitable for treating process fluids such as fluids used in the biopharmaceutical industry, e.g., fluids including desirable material such as proteinaceous material, for example, antibodies (e.g., monoclonal antibodies), or recombinant proteins such as growth factors.

The chromatography devices including the housings and the chromatography media can have any suitable configuration, including, but not limited to, configurations known in the art. For example, the chromatography media can be a membrane having one or more of the following forms: planar, pleated, hollow cylindrical, stacked, and spiral wound. Illustratively, in one embodiment, the membrane(s) can be in the form of a hollow, generally cylindrical, pleated element. In one embodiment, the chromatography media is a monolith having one or more of the following forms: disk, tube, and column.

Alternatively, or additionally, the test method disclosed herein may be used to determine the capacity of the chromatography media.

In one embodiment, the chromatography device comprises at least two different chromatography media, wherein at least one of the chromatography media is an ion exchange media. U.S. Pat. Publ. No. 2018-0257042 (Hester et al.), herein incorporated by reference, discloses a filtration media sequence comprising at least two different functionalized media in a particular order. For example, an ion exchange media in combination with a separation technique based on hydrophobic interaction, biospecific affinity, metal affinity, hydrophobic charge induction, thiophilic interactions, or combinations thereof. In one embodiment, as discussed in Hester et al., a nonwoven substrate functionalized with quaternary ammonium groups is located upstream of a microporous membrane functionalized with guanidyl groups. In one embodiment, the at least two different functionalized media are sealed in a housing as a pre-assembled device. The test method disclosed above can be useful for not only ensuring integrity, but also ensuring the chromatography device has the correct adsorbent capacity and/or number of layers.

In one embodiment, the chromatography system is calibrated for the second ion. By knowing the net breakthrough volume and the effective filter area, the dynamic binding capacity for the chromatography device in equivalents of the second ion per frontal media area can be calculated. This value can be compared to a known value of a reference device to ensure that the device possesses the expected adsorbent capacity.

When recovering and/or purifying biomaterials viral clearance is important. In other words, it is important to ensure that the eluate has a viral load below a particular threshold. Often viral clearance is conducted by testing the eluate for viral load, which is another process step and can be time consuming. In the present application, it has been discovered that the test method disclosed herein can be used as a faster method of assuring viral clearance. For example, a number of reference chromatography devices can be integrity tested according to the method disclosed herein. Some of the reference devices can be tested in their as-manufactured state, while others can be intentionally damaged, e.g., by creating holes in the media of various sizes, removing media layers during device construction, etc., prior to integrity testing. The undamaged and damaged devices can then be subsequently tested for viral clearance by processing of a fluid containing a known virus load. A relationship can then be made between measured integrity performance (e.g., net breakthrough value) and viral clearance performance (e.g., log reduction value of virus). This relationship can then be used to establish a criterion predicting the viral clearance performance of a future chromatography device of the same type based on its integrity test performance (e.g., net breakthrough value).

In one embodiment, the net breakthrough value can be compared to a known value of a reference device to determine viral clearance. As will be shown in the example below, a viral challenge was eluted through various chromatography media, some being compromised with needle holes. When the capacity for the second ion is within a certain range of a reference capacity value, the eluate has good viral clearance, for example above 2 or even 3 log reductions.

In one embodiment, the method disclosed herein may be used as a pre-use integrity test. Alternatively, or additionally, the method disclosed herein may be used as a post-use integrity test.

In one embodiment, the method disclosed herein may be used as a pre-use integrity test in combination with a gas pressure-based post-use integrity test. In other words, the test method disclosed herein is run on the chromatography device before processing the product-containing fluid, then the product containing fluid is passed through the chromatography device, followed by a gas pressure-based integrity test (such as ASTM F316-03 (2011) or ASTM D 6908-06 (2017)). In this embodiment, the integrity of the column can be tested before processing the product-containing fluid and the quality (e.g., mechanical integrity) of the chromatography device can be confirmed after processing the product-containing fluid to ensure no damage occurred during processing.

In one embodiment of the present disclosure, instructions containing the method disclosed herein are included with a chromatography device (or even chromatography media) either included in the same packaging as the chromatography device or sent separately. In one embodiment, the manufacturer provides the reference net breakthrough value and/or the expected adsorbent capacity.

TABLE 1

Exemplary Analyte Packages and Detectors for Integrity Testing of Anion Exchange Chromatography Devices

| Constituent(s) in First Solution | Constituent(s) in Challenge Solution | First Ion | Non-Binding Species | Second Ion | First Ion Relative Affinity Value | Second Ion Relative Affinity Value | Detector for Non-Binding Second Ion* | Detector for Second Species* |
|---|---|---|---|---|---|---|---|---|
| Sodium acetate | Potassium chloride | Acetate, $CH_3COO-$ | Potassium ion, $K^+$ | Chloride, $Cl^-$ | 3.2 | 22 | Potassium ISE | Chloride ISE |
| Potassium acetate | Sodium chloride | Acetate, $CH_3COO-$ | Sodium ion, $Na^+$ | Chloride, $Cl^-$ | 3.2 | 22 | Sodium ISE | Chloride ISE |
| Sodium carbonate or sodium bicarbonate | Potassium chloride | Bicarbonate, $HCO_3^-$ | Potassium ion, $K^+$ | Chloride, $Cl^-$ | 6 | 22 | Potassium ISE | Chloride ISE |
| Potassium carbonate or potassium bicarbonate | Sodium chloride | Bicarbonate, $HCO_3^-$ | Sodium ion, $Na^+$ | Chloride, $Cl^-$ | 6 | 22 | Sodium ISE | Chloride ISE |
| Sodium acetate | Potassium Iodide | Acetate, $CH_3COO-$ | Potassium ion, $K^+$ | Iodide, $I^-$ | 3.2 | 175 | Potassium ISE | Iodide ISE |
| Potassium acetate | Sodium iodide | Acetate, $CH_3COO-$ | Sodium ion, $Na^+$ | Iodide, $I^-$ | 3.2 | 175 | Sodium ISE | Iodide ISE |

TABLE 1-continued

Exemplary Analyte Packages and Detectors for Integrity Testing of Anion Exchange Chromatography Devices

| Constituent(s) in First Solution | Constituent(s) in Challenge Solution | First Ion | Non-Binding Species | Second Ion | First Ion Relative Affinity Value | Second Ion Relative Affinity Value | Detector for Non-Binding Second Ion* | Detector for Second Species* |
|---|---|---|---|---|---|---|---|---|
| Sodium carbonate or sodium bicarbonate | Potassium Iodide | Bicarbonate, $HCO_3^-$ | Potassium ion, $K^+$ | Iodide, $I^-$ | 6 | 175 | Potassium ISE | Iodide ISE |
| Sodium carbonate or sodium bicarbonate | Sodium iodide | Bicarbonate, $HCO_3^-$ | Sodium ion, $Na^+$ | Iodide, $I^-$ | 6 | 175 | Sodium ISE | Iodide ISE |
| Sodium chloride | Potassium Iodide | Chloride, $Cl^-$ | Potassium ion, $K^+$ | Iodide, $I^-$ | 22 | 175 | Potassium ISE | Iodide ISE |
| Potassium chloride | Sodium iodide | Chloride, $Cl^-$ | Sodium ion, Na+ | Iodide, $I^-$ | 22 | 175 | Sodium ISE | Iodide ISE |
| Sodium sulfate | Potassium Iodide | Sulfate, $SO_4^{2-}$ | Potassium ion, $K^+$ | Iodide, $I^-$ | 150 | 175 | Potassium ISE | Iodide ISE |
| Potassium sulfate | Sodium iodide | Sulfate, $SO_4^{2-}$ | Sodium ion, $Na^+$ | Iodide. $I^-$ | 150 | 175 | Sodium ISE | Iodide ISE |

*"ISE" is an abbreviation for "ion selective electrode." In all cases in which ISE's are listed, a different detector, such as a UV or conductivity detector, may be used.

TABLE 2

Exemplary Analyte Packages and Detectors for Integrity Testing of Cation Exchange Chromatography Devices

| Constituent(s) in First Solution | Constituent(s) in Challenge Solution | First Ion | Non-Binding Species | Second Ion | First Ion Relative Affinity Value | Second Ion Relative Affinity Value | Detector for Non-Binding Second Ion* | Detector for Second Species* |
|---|---|---|---|---|---|---|---|---|
| Lithium acetate, carbonate, nitrate, sulfate, bromide, fluoride, or iodide | Potassium chloride | Lithium ion, $Li^+$ | Chloride, $Cl^-$ | Potassium ion, $K^+$ | 1 | 2.9 | Chloride ISE | Potassium ISE |
| Lithium acetate, carbonate, nitrate, sulfate, bromide, fluoride, or iodide | Sodium chloride | Lithium ion, $Li^+$ | Chloride, $Cl^-$ | Sodium ion, $Na^+$ | 1 | 1.98 | Chloride ISE | Sodium ISE |
| Sodium acetate, carbonate, bicarbonate, nitrate, sulfate, bromide, fluoride, or iodide | Potassium chloride | Sodium ion, $Na^+$ | Chloride, $Cl^-$ | Potassium ion, $K^+$ | 1.98 | 2.9 | Chloride ISE | Potassium ISE |
| Lithium acetate, carbonate, nitrate, sulfate, chloride, fluoride, or iodide | Potassium bromide | Lithium ion, $Li^+$ | Bromide, $Br^-$ | Potassium ion, $K^+$ | 1 | 2.9 | Bromide ISE | Potassium ISE |
| Lithium acetate, carbonate, nitrate, sulfate, chloride, fluoride, or iodide | Sodium bromide | Lithium ion, $Li^+$ | Bromide, $Br^-$ | Sodium ion, $Na^+$ | 1 | 1.98 | Bromide ISE | Sodium ISE |
| Sodium acetate, carbonate, nitrate, sulfate, bicarbonate, chloride, fluoride, or iodide | Potassium bromide | Sodium ion, $Na^+$ | Bromide, $Br^-$ | Potassium ion, $K^+$ | 1.98 | 2.9 | Bromide ISE | Potassium ISE |
| Lithium acetate, carbonate, nitrate, sulfate, chloride, bromide, or iodide | Potassium fluoride | Lithium ion, $Li^+$ | Fluoride, $F^-$ | Potassium ion, $K^+$ | 1 | 2.9 | Fluoride ISE | Potassium ISE |
| Lithium acetate, carbonate, nitrate, sulfate, chloride, bromide, or iodide | Sodium fluoride | Lithium ion, $Li^+$ | Fluoride, F- | Sodium ion, Na+ | 1 | 1.98 | Fluoride ISE | Sodium ISE |
| Sodium acetate, carbonate, bicarbonate, nitrate, sulfate, chloride, bromide, or iodide | Potassium fluoride | Sodium ion, $Na^+$ | Fluoride, $F^-$ | Potassium ion, $K^+$ | 1.98 | 2.9 | Fluoride ISE | Potassium ISE |
| Lithium acetate, carbonate, nitrate, sulfate, chloride, bromide, or fluoride | Potassium iodide | Lithium ion, $Li^+$ | Iodide, $I^-$ | Potassium ion, $K^+$ | 1 | 2.9 | Iodide ISE | Potassium ISE |
| Lithium acetate, carbonate, nitrate, sulfate, chloride, bromide, or fluoride | Sodium iodide | Lithium ion, $Li^+$ | Iodide, $I^-$ | Sodium ion, $Na^+$ | 1 | 1.98 | Iodide ISE | Sodium ISE |
| Sodium acetate, carbonate, bicarbonate, nitrate, sulfate, chloride, bromide, or fluoride | Potassium iodide | Sodium ion, $Na^+$ | Iodide, $I^-$ | Potassium ion, $K^+$ | 1.98 | 2.9 | Iodide ISE | Potassium ISE |
| Lithium acetate, carbonate, nitrate, sulfate, bromide, fluoride, or iodide | Calcium chloride | Lithium ion, $Li^+$ | Chloride, $Cl^-$ | Calcium ion, $Ca^{2+}$ | 1 | 5.16 | Chloride ISE | Calcium ISE |

TABLE 2-continued

Exemplary Analyte Packages and Detectors for Integrity Testing of Cation Exchange Chromatography Devices

| Constituent(s) in First Solution | Constituent(s) in Challenge Solution | First Ion | Non-Binding Species | Second Ion | First Ion Relative Affinity Value | Second Ion Relative Affinity Value | Detector for Non-Binding Second Ion* | Detector for Second Species* |
|---|---|---|---|---|---|---|---|---|
| Sodium acetate, carbonate, bicarbonate, nitrate, sulfate, bromide, fluoride, or iodide | Calcium chloride | Sodium ion, $Na^+$ | Chloride, $Cl^-$ | Calcium ion, $Ca^{2+}$ | 1.98 | 5.16 | Chloride ISE | Calcium ISE |
| Potassium acetate, carbonate, bicarbonate, nitrate, sulfate, bromide, fluoride, or iodide | Calcium chloride | Potassium ion, $K^+$ | Chloride, $Cl^-$ | Calcium ion, $Ca^{2+}$ | 2.9 | 5.16 | Chloride ISE | Calcium ISE |

*"ISE" is an abbreviation for "ion selective electrode." In all cases in which ISE's are listed, a different detector, such as a UV or conductivity detector, may be used.

EXAMPLES

Unless otherwise noted, all parts, percentages, ratios, etc. in the examples and the rest of the specification are by weight, and all reagents used in the examples were obtained, or are available, from general chemical suppliers such as, for example, Sigma-Millipore, Saint Louis, Missouri, or may be synthesized by conventional methods.

The following abbreviations are used in this section: h=hour, mL=milliliter, rpm=revolutions per minute, min=minute, M=molar, mM=millimolar, g/mol=gram per mole, Ga=gauge, equiv=equivalent, and cm=centimeter.

| MATERIALS | |
|---|---|
| Trade Designation/ Abbreviation | Description |
| DI | Deionized water from Millipore Milli Q Water Purification Lab Unit |
| NaAc | Sodium acetate, anhydrous ($CH_3COONa$), CAS No. 127-09-3, 82.03 g/mol |
| AcOH | Acetic acid, glacial ($CH_3COOH$), CAS No. 64-19-7 |
| KCl | Potassium chloride (KCl), CAS No. 7447-40-7, 74.5513 g/mol |
| ORION IONPLUS OPTIMUM RESULTS B | Filling solution for chloride ion selective electrode, available from Thermo Fisher Scientific. Waltham, MA, USA |
| ORION IONPLUS OPTIMUM RESULTS E | Filling solution for potassium ion selective electrode, available from Thermo Fisher |
| FNW | Quaternary ammonium functional nonwoven preparable as described in Example 1 of U.S. Pat. No. 9,821,276, the disclosure of which is incorporated herein by reference in its entirety. |
| GFM | Guanidinium-functional membrane preparable as described in Example 42 of U.S. Patent Application Publication No. 2012/0252091, the disclosure of which is incorporated herein by reference in its entirety. |
| ZPN020 | A non-functionalized, asymmetric nylon-6,6 microporous membrane having a qualifying pore rating of 0.2 microns, grade designation ZPN020, available from 3M Company |
| PES filter | Polyethersulfone filter having a pore size rating of 0.2 microns available from 3M Co., Maplewood, MN |
| LiAc | Lithium acetate |
| NaCl | Sodium chloride |
| Tris | TRIS base available under the trade designation "J.T BAKER" from Thermo Fischer Scientific Company, Waltham, MA |
| $MgSO_4$ | Magnesium sulfate |
| HCl | Hydrochloric acid |
| PHI X174 ATCC 13706-B1 | *Escherichia coli* bacteriophage Phi X174, available from ATCC, Manassas, VA, USA |
| *E. coli* C | *Escherichia coli* C (Migula) Castellani and Chalmers (ATCC 13706), available from ATCC |
| DIFCO Nutrient Broth | Nutrient broth, available from BD Biosciences, San Jose, CA, USA |
| DIFCO Nutrient Agar | Nutrient agar, available from BD Biosciences |
| DIFCO Tryptic Soy Broth | Culture broth, available from BD Biosciences |
| DIFCO Tryptic Soy Agar | Culture agar, available from BD Biosciences |
| Agarose | Agarose Type III-A, High EEO (CAS 9012-36-6), available from Sigma-Millipore |

| EQUIPMENT | |
|---|---|
| Model/Description | Supplier |
| AKTA AVANT chromatography system | GE Healthcare, Chicago, IL, USA |
| AKTA PURE protein purification system | GE Healthcare |
| I/O-box E9 external unit controller, Product No. 29-0113-61 | GE Healthcare |
| ThermoFisher Sure-Flow Combination Potassium Ion Selective Electrode (ISE), Item No. 9719BNWP | Thermo Fisher |
| ThermoFisher Sure-Flow Combination Solid State Chloride Ion Selective Electrode (ISE), Item No. 9617BNWP | Thermo Fisher |
| Plexiglass Flow Cell for Combination Ion Selective Electrode, Item No. 79010 | FIAlab Instruments, Inc., Seattle, WA, USA |
| Cable with 2 BNC female jacks, part number. 290-1009-ND | Digi-Key Co., Thief River Falls, MN, USA |
| Interconnect jack, BNC female to BNC female, part number ARF1069-ND | Digi-Key Co. |
| 25-mm diameter screw-together filter housing with an effective frontal filtration area of 2.84 cm$^2$ | Mathias Die Company, St. Paul, MN |
| Cation exchange column having a resin volume of 1 mL, commercially available under the trade designation HITRAP SP XL | GE Healthcare |
| Tangential flow filtration process system, commercially available under the trade designation PENDOTECH TFF PROCESS CONTROL SYSTEM | PendoTech, Princeton, NJ, USA |
| Instrument control commercially available under the trade designation PENDOTECH PENDOKIT Solution | PendoTech |
| SPECTRA-POR FLOAT-A-LYZER G2 Dialysis Device 100kD | Repligen, Waltham, MA, USA |
| Phosphate buffered saline solution (PBS), pH 7.4 | Thermo Fisher |

Solutions

The following aqueous solutions in deionized water were prepared using standard techniques and unless otherwise noted, they were filtered through a sterile filter and stored prior to use.

ISE Storage Solution: 10 mM Potassium Chloride
First Solution A: 0.5 M Sodium Acetate Buffer, pH 7
First Solution B: 0.5 mM Lithium Acetate
First Solution C: 1 M Sodium Acetate
Wash Solution: 20 mM Sodium Acetate
Wash Solution 2: 20 mM Lithium Acetate
Challenge Solution: 20 mM Potassium Chloride
Dialysis Buffer a 20 mM solution of TrisHCl, pH 7.5, containing 10 mM NaCl and 8 mM MgSOs.

Bacteriophage Solutions

All liquid and agar media were prepared following the manufacturer's instructions.

E. coli Stock: a nutrient broth agar plate was prepared according to the manufacturer's instruction. E. coli C (ATCC 13706) was streaked onto the plate. A nutrient broth media was prepared by combining 0.8 g of BD DIFCO Nutrient Broth and 0.5 g of Sodium Chloride. An E. coli Stock solution was placed in the nutrient broth media and allowed to grow for about 22-26 hours at a temperature of about 37° C.

Preparation of Bacteriophage Phi X174 Stock Solution: Bacteriophage Phi X174 stock solution was prepared in clarified broth cultures and purified using dialysis. An E. coli C culture was prepared following supplier's instructions and grown overnight. Resulting optical density of the culture at a wavelength of 600 nm (OD600) was around 1.8-2.0.

Approximately 0.1 L of nutrient broth media was prepared by combining 0.8 g of BD DIFCO Nutrient Broth and 0.5 g of Sodium Chloride. The nutrient broth media was then seeded with 2.5% (v/v) of the E. coli C culture.

The seeded nutrient broth was maintained at a temperature of about 37° C. and under agitation of about 210 rpm until a cell density of approximately 10$^8$ live bacteria/mL (OD600 approx. 0.45-0.5) was achieved. About 10$^8$-10$^9$ PFU (plaque-forming units) of Phi X174 were added to E. coli C culture and allowed to propagate in the bacterial culture for 3-6 h at 37° C. under agitation (210 rpm).

Optical density of culture was checked every hour. When the OD600 became smaller of original density by 0.1 unit the bacterial culture was harvested and centrifuged at moderate speed (10 000 rpm in an Allegra 64R centrifuge) for 15 min to pellet bacteria and debris.

Supernatant was filtered with a PES filter having a pore size rating of 0.2 microns. The filtered supernatant was subsequently purified by dialysis at 4 C using a magnetic stir plate operating at 50 rpm. The volume of the Dialysis Buffer solution was 100 times larger than the sample volume.

The Dialysis Buffer solution was changed three times in a 24-hour period. Titer of phage was determined according to the manufacturer's (ATTC) instructions. Usual titer of Phi X174 was 0.5×10$^{10}$ PFU/mL.

Preparation of Bacteriophage Phi X174 Challenge Solution: Phage challenge solutions were created by diluting the concentrated Phi X174 stock into 50 mM Tris Buffer (pH 7.5) to reach a goal of 1×10$^7$ PFU/mL.

Testing Conditions

Chromatography system setup: The I/O-box E9 external unit controller was installed on the chromatography system (AKTA Avant) and configured according to the manufacturer's instructions. The potassium and chloride ISE's were connected to the I/O-box E9, using the BNC cable and BNC interconnect jacks, according to the manufacturer's instructions.

An ISE probe fixture assembly was constructed by taping together the two plexiglass ISE flow cells and connecting the outlet of the first flow cell to the inlet of the second flow cell with a minimal length of small diameter tubing. The inlet of the first flow cell was connected with tubing to an outlet valve on the chromatography system. The potassium and chloride ISE's were each filled with the appropriate filling solution, according to the manufacturer's instructions, rinsed with deionized water, and mounted in the ISE probe fixture assembly.

Anion Exchange Setup:

The chromatography device comprising the anion exchange media was connected to a column position of the chromatography system. The ISE probe fixture assembly was filled and flushed with Wash Solution until the ISE probe signals stabilized. When the ISE's were not in use, they were removed from the ISE probe fixture assembly and immersed in containers of the ISE Storage Solution (10 mM KCl).

Cation Exchange Setup:

The chromatography device comprising cation exchange media was connected to a column position of the chromatography system. The ISE probe fixture assembly was filled and flushed with Wash Solution 2 until the ISE probe signals stabilized.

The cation exchange column was flushed with 10 mL of First Solution B at a flow rate of 2 mL/min to equilibrate the column with lithium acetate. During this equilibration step, the eluate was directed to waste. The cation exchange column was then washed with 10 mL of Wash Solution 2 at a flow rate of 2 mL/min with the eluate directed to waste. After this initial wash period, the eluate was directed to the ISE probe fixture assembly and flushing with Wash Solution 2 at 2 mL/min was continued until the ISE probe signals stabilized (about 5 mL). The flow rate was then dropped to 1 mL/min and flushing with Wash Solution 2 was continued until the probe signals again stabilized (about 2 mL). Finally, the chromatography device was flushed with Challenge Solution at a flow rate of 1 mL/min. The potassium and chloride ISE signals were monitored during this challenge period.

Calibration of the ISE's

In some examples, the ISE's were calibrated by running gradients of the Challenge Solution and deionized water at a flow rate of 3 mL/min with the outlet flow directed through the ISE probe fixture assembly. Gradients of 100%, 75%, 50%, and 25% of the Challenge Solution were run, resulting in KCl solution concentrations of 20, 15, 10, and 5 mM, respectively. At each gradient setting, the mV response of each of the probes was recorded at the appropriate KCl concentration. A log-linear plot of KCl concentration vs. mV response was prepared and the calibration data for each of the ISE's was fit by regression analysis to a best-fit Equation 1, $$[I] = Ae^{Bx} \quad \text{(Equation 1)}$$

Where [I] is the concentration of $K^+$ or $Cl^-$ ions in (mM), x is the ISE response (mV), and A and B are calibration coefficients. The calibration coefficients for $K^+$ ion was A=10.17 and B=0.11 (correlation of 0.991). The calibration coefficients for $Cl^-$ ion was A=15.31 and B=−0.0593 (correlation of 0.998).

In some of the examples below, $K^+$ and $Cl^-$ concentrations were obtained by applying Equation (1) to the mV responses of the potassium and Chloride ISE's, respectively. In other examples, the calibration was not used and breakthrough values were obtained directly from the raw ISE responses measured in millivolts.

Examples

Test Method

The following test method was used in Examples 1-8.

Step 1: The capsule was flushed with 24 mL of the First Solution A at a flow rate of 12 mL/min with the eluate directed to waste.

Step 2: The capsule was flushed with 12 mL of Wash Solution at a flow rate of 6 mL/min with the eluate directed to waste.

Step 3: The capsule was flushed with another 12 mL of Wash Solution at a flow rate of 3 mL/min with the eluate directed to the ISE fixture assembly. This resulted in a stable mV reading from each of the ISE's, toward the end of this step, indicative of substantially zero $K^+$ and $Cl^-$ ion concentration in the eluate.

Step 4: The capsule was flushed with 30 mL of Challenge Solution at a flow rate of 3 mL/min with the eluate directed to the ISE fixture assembly. After each approximately 0.008 mL increment of fluid had passed through the capsule, the mV reading of each of the ISE's was recorded automatically by the chromatography device's software.

Step 5: Equation (1), containing the appropriate calibration coefficients for each ISE, was applied to each of the mV readings for each of the ISE's to obtain a concentration of $K^+$ or $Cl^-$ ions in millimolar (mM).

Example 1

Capsule 1 was prepared by assembling, in a 25 mm diameter filter housing, four disc layers of FNW, each disc having a diameter of 25 mm, and a single 25 mm-diameter disc of ZPN020 downstream of the four disc layers of FNW. Capsule 1 had an effective filtration area of 2.84 $cm^2$. The Test Method described above was performed on Capsule 1, two times sequentially.

Capsule 2 was prepared as described above for Capsule 1, except that the capsule included four disc layers of FNW, and 3 disc layers of GFM downstream of the four disc layers of FNW. Capsule 2 had an effective filtration area of 2.84 $cm^2$. The Test Method described above was performed on Capsule 2, three times sequentially.

Figure 3:
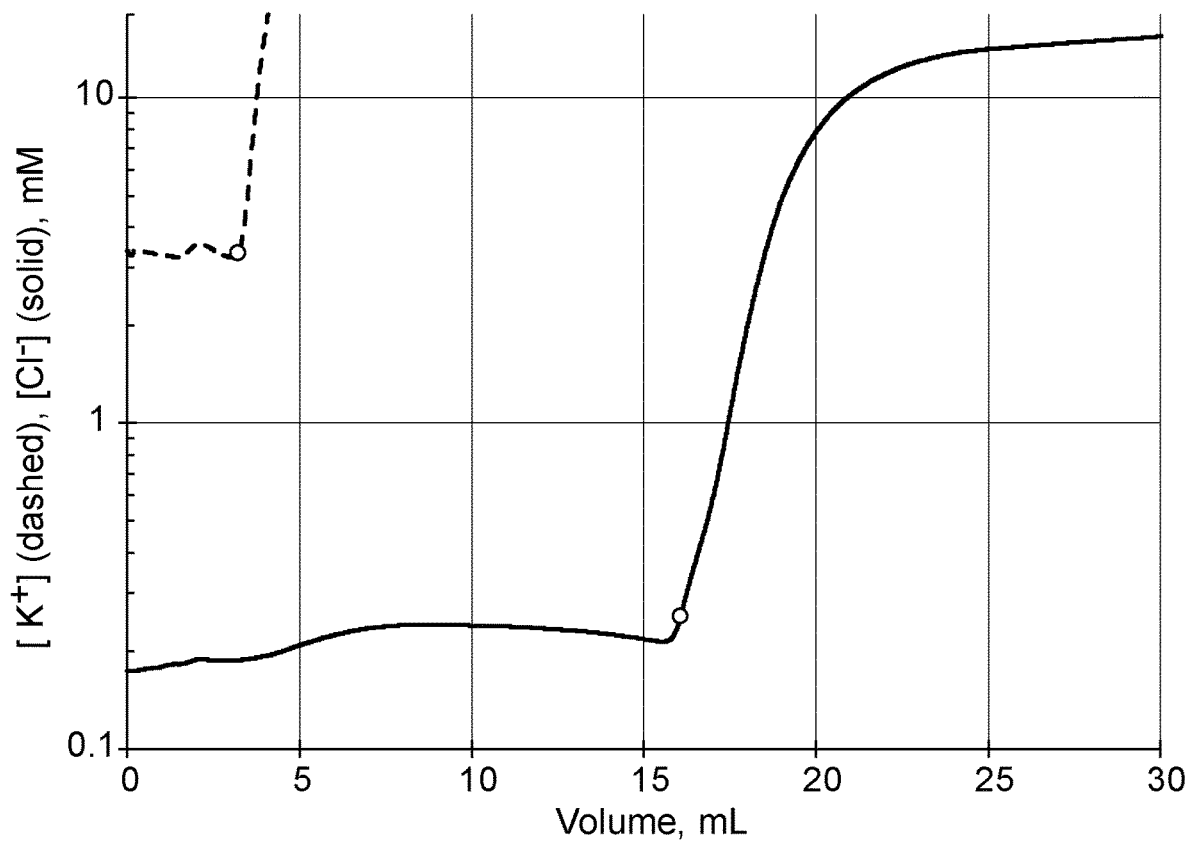
FIG. 3 is a chromatogram of Example 1 showing where the breakthrough value was for trial 1 in Example 1.

An exemplary plot of ion concentration vs. eluate volume is shown in FIG. 3, wherein the curve for $K^+$ ions is shown in as a dashed line, and the curve for $Cl^-$ ions shown as a solid line. The chromatograms were plotted on a log-linear scale. Selected breakthrough points are shown as circular symbols.

Breakthrough Volumes (BV) were calculated based on the selected breakthrough points. Net Breakthrough Volume (NBV) was calculated by subtracting the Breakthrough Volume for potassium ions from the Breakthrough Volume for chloride ions. Dynamic Binding Capacity (DBC) was calculated using the known KCl concentration of the Challenge Solution and the effective filtration area of the capsule following Equation (2). Results are summarized in Table 2, below.

$$\text{Capacity } [eq/m^2] = \frac{\text{Net breakthrough volume [mL]}}{2.84 \text{ cm}^2} \times \frac{1 \text{ L}}{1000 \text{ mL}} \times \frac{\frac{20}{1000} \text{mol}}{1 \text{ L}} \times \frac{1 \text{ eq}}{1 \text{ mol}} \times \frac{(100)^2 \text{ cm}^2}{1 \text{ m}^2} \quad \text{(Equation 2)}$$

TABLE 2

| Capsule | Replicates | K+ BV (mL) | Cl− BV (mL) | NBV (mL) | Cl− DBC (equiv/m²) |
|---|---|---|---|---|---|
| Capsule 1 | 1 | 3.30 | 12.52 | 9.22 | 0.649 |
|  | 2 | 3.38 | 12.55 | 9.17 | 0.646 |
| Capsule 2 | 1 | 3.33 | 16.07 | 12.73 | 0.897 |
|  | 2 | 3.59 | 16.37 | 12.78 | 0.900 |
|  | 3 | 3.53 | 16.41 | 12.87 | 0.907 |

Results show that media constructions of different types, having different quantities of ion exchange functionality, result in different chloride dynamic binding capacities. Moreover, the test method is non-destructive and repeatable, resulting in similar results for a given capsule over multiple trials.

Example 2

Example 2 illustrates a method according to the present application, to determine whether the capsule being tested contains the expected ion exchange functionality. After performing the three sequential runs in Example 1, Capsule 2's housing was opened and a single disc layer of FNW was removed from the upstream side of the capsule construction and discarded. The housing was then closed and the test method was repeated.

The process of removing individual media disc layers from the upstream side of the capsule and testing the capsule was repeated until the housing was empty.

Figure 4:
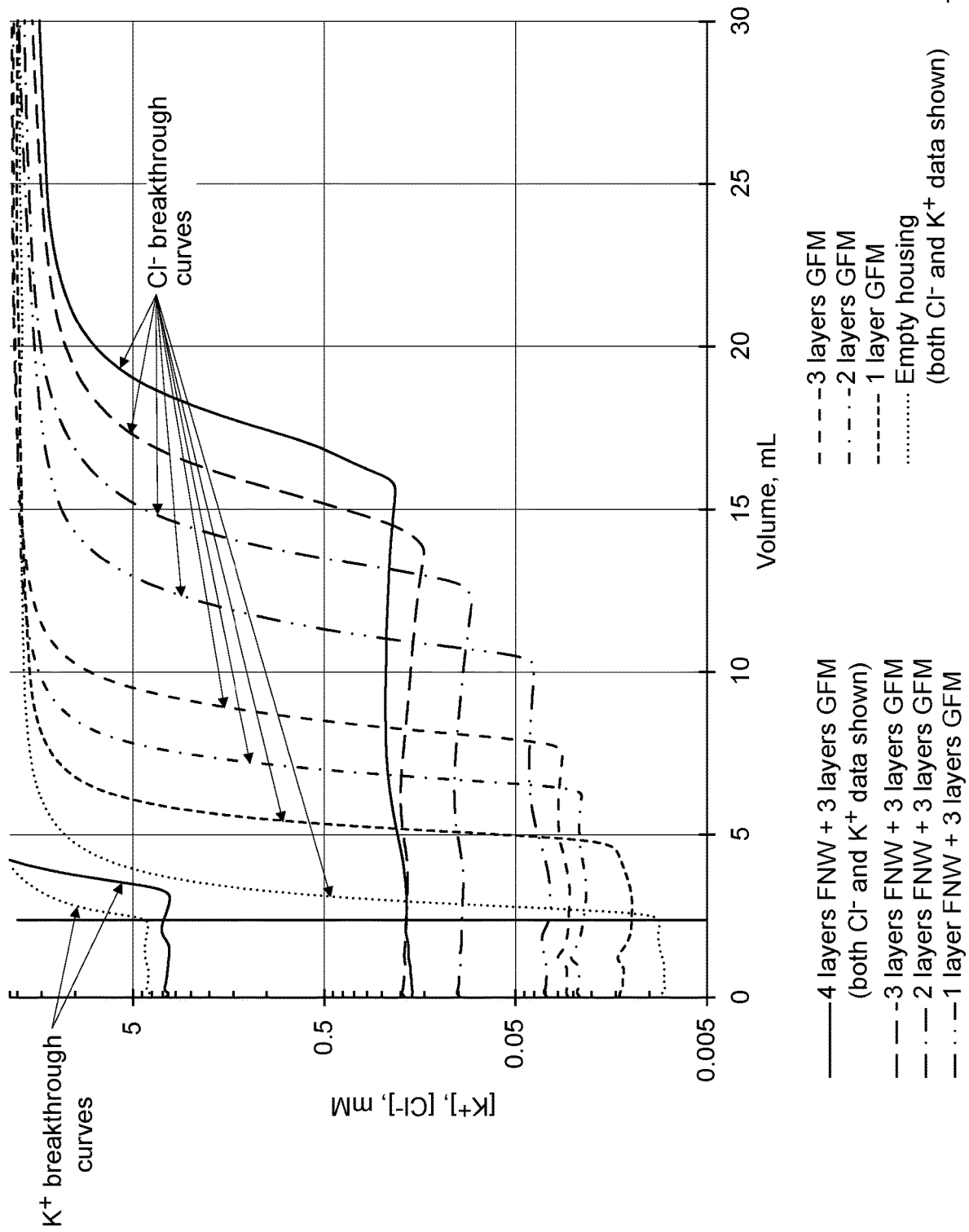
FIG. 4 is the chromatogram of Example 2 showing the concentration of potassium ion and chloride ion versus elution volume for various runs using two ion selective electrodes.

Data analysis was performed as described in Example 1. Breakthrough curves are shown in FIG. 4. Numerical results are summarized in Table 3.

TABLE 3

| Capsule Construction | Replicates | K+ BV (mL) | Cl− BV (mL) | NBV (mL) | Cl− DBC (equiv/m²) |
|---|---|---|---|---|---|
| Capsule 2 (4 FNW layers/3 GFM layers) | 1 | 3.33 | 16.07 | 12.73 | 0.897 |
|  | 2 | 3.59 | 16.37 | 12.78 | 0.900 |
|  | 3 | 3.53 | 16.41 | 12.87 | 0.907 |
| 3 FNW layers/ 3 GFM layers | 1 | 3.26 | 14.16 | 10.90 | 0.768 |
| 2 FNW layers/ 3 GFM layers | 1 | 3.18 | 12.75 | 9.57 | 0.674 |
| 1 FNW layer/ 3 GFM layers | 1 | 3.14 | 10.47 | 7.34 | 0.517 |
| 3 GFM layers | 1 | 2.71 | 7.68 | 4.98 | 0.350 |
| 2 GFM layers | 1 | 2.67 | 6.42 | 3.75 | 0.264 |
| 1 GFM layer | 1 | 2.63 | 4.67 | 2.03 | 0.143 |
| Empty capsule | 1 | 2.37 | 2.46 | 0.09 | 0.006 |

Example 3

Example 3 illustrates the use of the method to show that a modified capsule was non-integral.

A 16-Ga syringe needle was obtained, and its pointed tip cut off using a pair of cutting pliers. After performing the three sequential runs in Example 1, Capsule 1's housing was opened, and the blunted syringe needle used to punch a single 16-Ga hole through the entire media stack. The damaged media stack was subsequently re-sealed inside the housing to create a non-integral capsule, hereinafter referred to as Capsule 1A. The non-integral capsule (Capsule 1A) was subjected to the test method described in Example 1, above. The breakthrough values and the dynamic binding capacity for the chloride ion are summarized in Table 4, below.

TABLE 4

| Capsule Construction | Replicates | K− BV (mL) | Cl− BV (mL) | NBV (mL) | Cl− DBC (equiv/m²) |
|---|---|---|---|---|---|
| Capsule 1 | 1 | 3.30 | 12.52 | 9.22 | 0.649 |
|  | 2 | 3.38 | 12.55 | 9.17 | 0.646 |
| Capsule 1A | 1 | 2.49 | 3.38 | 0.88 | 0.062 |

Example 4

Example 4 illustrates the use of the method to discover multiple types of defects in the capsules resulting in media bypass.

Two additional Capsule 2 constructions were prepared as described in Example 1, above, and are hereinafter referred to as Capsule 2a and Capsule 2b. The three capsules were tested using the procedure described in Example 1, above.

The pointed tips of 16-Ga and 22-Ga syringe needles were cut off using cutting pliers. These syringes were used to modify Capsules 2a and 2b.

For Capsule 2a, the blunted 22-Ga syringe needle was used to punch a 22-Ga hole through the 3 GFM layers only of Capsule 2a. The capsule was re-assembled and is hereinafter referred to as Capsule 2aA. Capsule 2aA was tested using the procedure described in Example 1, above.

Capsule 2aA was opened a second time and the 22-Ga syringe was used to punch through the 4 FNW layers. The capsule was re-assembled and is hereinafter referred to as Capsule 2aB. Capsule 2aB was tested using the procedure described in Example 1, above.

Capsule 2b was opened and the blunted 16-Ga syringe needle was used to punch a 16-Ga hole through the 4 FNW layers only of Capsule 2b. The capsule was re-assembled and is hereinafter referred to as Capsule 2bC. Capsule 2bC was tested using the procedure described in Example 1, above.

Capsule 2bC was then opened again and the blunted 22-Ga syringe needle was used to punch a 22-Ga hole through the 3 GFM layers. The capsule was re-assembled and is hereinafter referred to as Capsule 2bD. Capsule 2bD was tested using the procedure described in Example 1, above.

Data analysis was performed as described in Example 1. The breakthrough values and the dynamic binding capacity for the chloride are summarized in Table 5, below.

TABLE 5

| Capsule Construction | Replicates | K+ BV (mL) | Cl− BV (mL) | NBV (mL) | Cl− DBC (equiv/m²) |
|---|---|---|---|---|---|
| Capsule 2a | 1 | 3.33 | 16.79 | 13.46 | 0.948 |
| Capsule 2aA | 1 | 3.11 | 10.03 | 6.92 | 0.487 |
| Capsule 2aB | 1 | 3.10 | 9.34 | 6.24 | 0.439 |
| Capsule 2b | 1 | 3.46 | 17.42 | 13.96 | 0.983 |
| Capsule 2bC | 1 | 2.75 | 8.22 | 5.47 | 0.385 |
| Capsule 2bD | 1 | 2.85 | 4.02 | 1.17 | 0.083 |

Example 5

This example illustrates the use of the method to assess the integrity and quantify the cation exchange capacity of a cation exchange device. The cation exchange chromatography setup was used.

Chloride and potassium ISE responses were determined. A breakthrough criterion for each ISE signal was established, such that the challenge volume at which the ISE response departed by 1% from the average baseline response value prior to the inflection was defined as the breakthrough volume for the corresponding ion. The Cl— breakthrough volume was then subtracted from the K+ breakthrough volume to obtain the net breakthrough volume. The known KCl concentration of the Challenge Solution (20 mM) and the resin volume of the cation exchange device (1 mL) were then used to calculate the potassium dynamic binding capacity of the capsule in equivalents of potassium per liter of resin volume, according to Equation 3:

$$\text{Capacity }[eq/L] = \frac{\text{Net breakthrough volume [mL]}}{1 \text{ ml}} \times \frac{1000 \text{ mL}}{1 \text{ L}} \times \frac{1 \text{ L}}{1000 \text{ mL}} \times \frac{\frac{20}{1000} eq}{1 \text{ L}} \quad \text{(Equation 3)}$$

Results are summarized in Table 6, below.

TABLE 6

| | |
|---|---|
| Cl⁻ BV (mL) | 1.53 |
| K⁺ BV (mL) | 10.63 |
| NBC (mL) | 9.10 |
| K⁺ DBC (equiv/L) | 0.182 |

Example 6

Example 6 demonstrated the use of a detector other than an ion selective electrode to determine one of the breakthrough events when using the method disclosed herein. Additionally, this example illustrates that optional calibration of ISE's is unnecessary to use the inventive method; ISE's can be used to detect breakthrough events based on raw changes in the electrode potentials of the ISE's.

A protein purification chromatography system (AKTA Pure) was setup with an I/O-box E9 external unit controller connected to potassium and chloride ISE's mounted in an ISE probe fixture assembly connected to an outlet of the chromatography system. A sealed anion exchange capsule having an effective frontal surface area of 3.2 cm² was constructed, the anion exchange capsule comprising 4 layers of FNW layers upstream of 3 layers of GFM layers. The anion exchange capsule was connected to a column position of the chromatography system.

The chromatography system fluid paths were filled with each of the solutions according to standard liquid chromatography practices. The ISE probe fixture assembly was filled and flushed with Wash Solution until the ISE probe signals stabilized. The chromatography system had an inline UV monitor capable of monitoring UV adsorption at 280 nm at a position downstream of the anion exchange capsule and upstream of the ISE probe fixture assembly. The chromatography system also had a conductivity probe similarly situated.

The anion exchange capsule was flushed with 9 mL of First Solution C at a flow rate of 14 mL/min to bind acetate to substantially all the anion exchange groups of the media. During this equilibration step, the eluate was directed to waste. The ion exchange column was then washed with Wash Solution at a flow rate of 10.5 mL/min, with the eluate directed to waste, until the outlet conductivity probe measured a conductivity less than 7 mS/cm (about 16 mL). After this initial wash period, the eluate was directed to the ISE probe fixture assembly, and flushing with 14 mL of Wash Solution at 10.5 mL/min was continued after which the ISE probes stabilized. Finally, the anion exchange capsule was challenged with Challenge Solution at a flow rate of 10.5 mL/min. The potassium and chloride ISE signals, as well as the UV and conductivity signals, were monitored during this challenge period.

Figure 5:
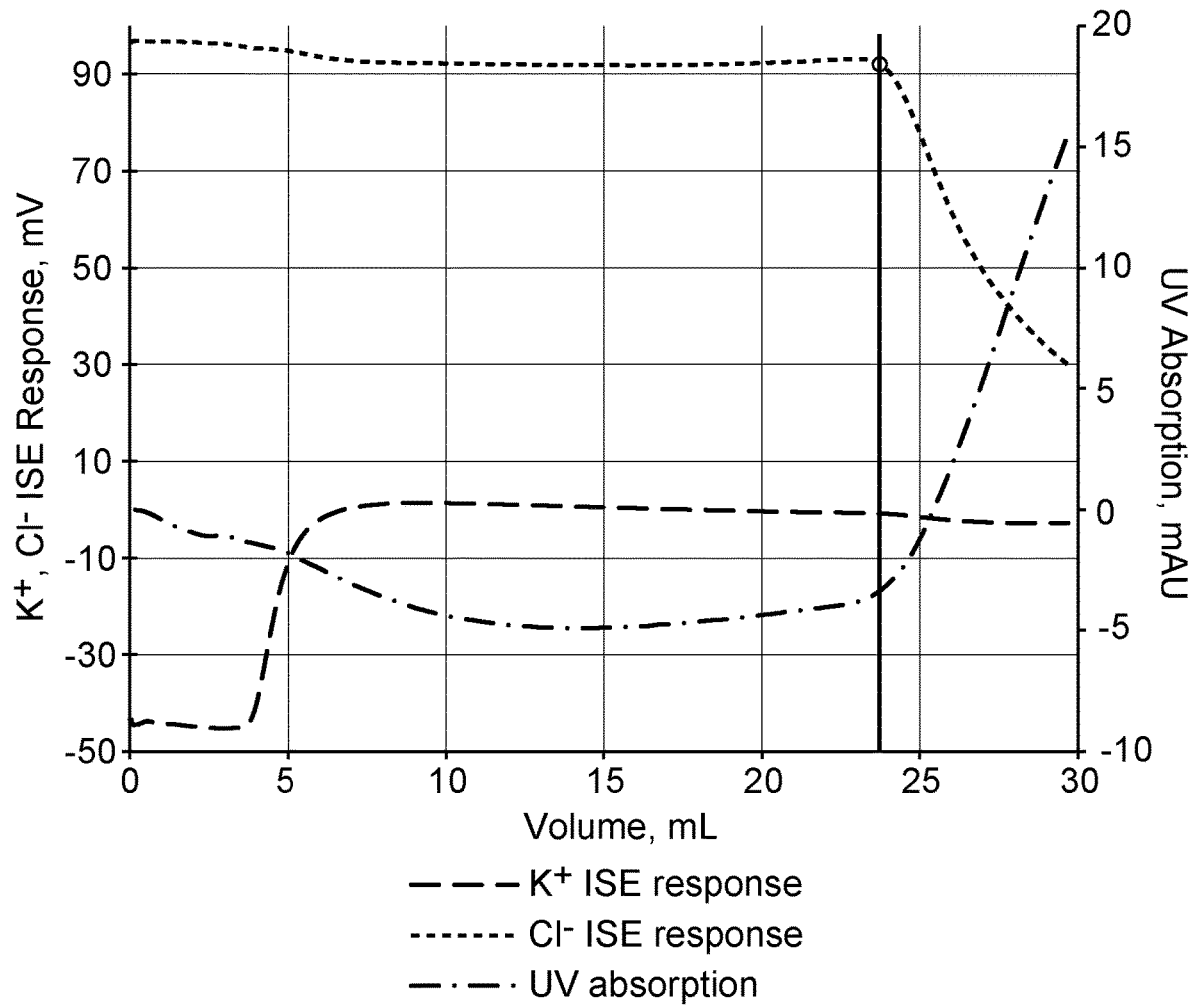
FIG. 5 is the chromatogram of Example 6 showing the concentration of potassium ion and chloride ion versus elution volume for a cation exchange media using two ion selective electrodes and a UV detector.
Figure 6:
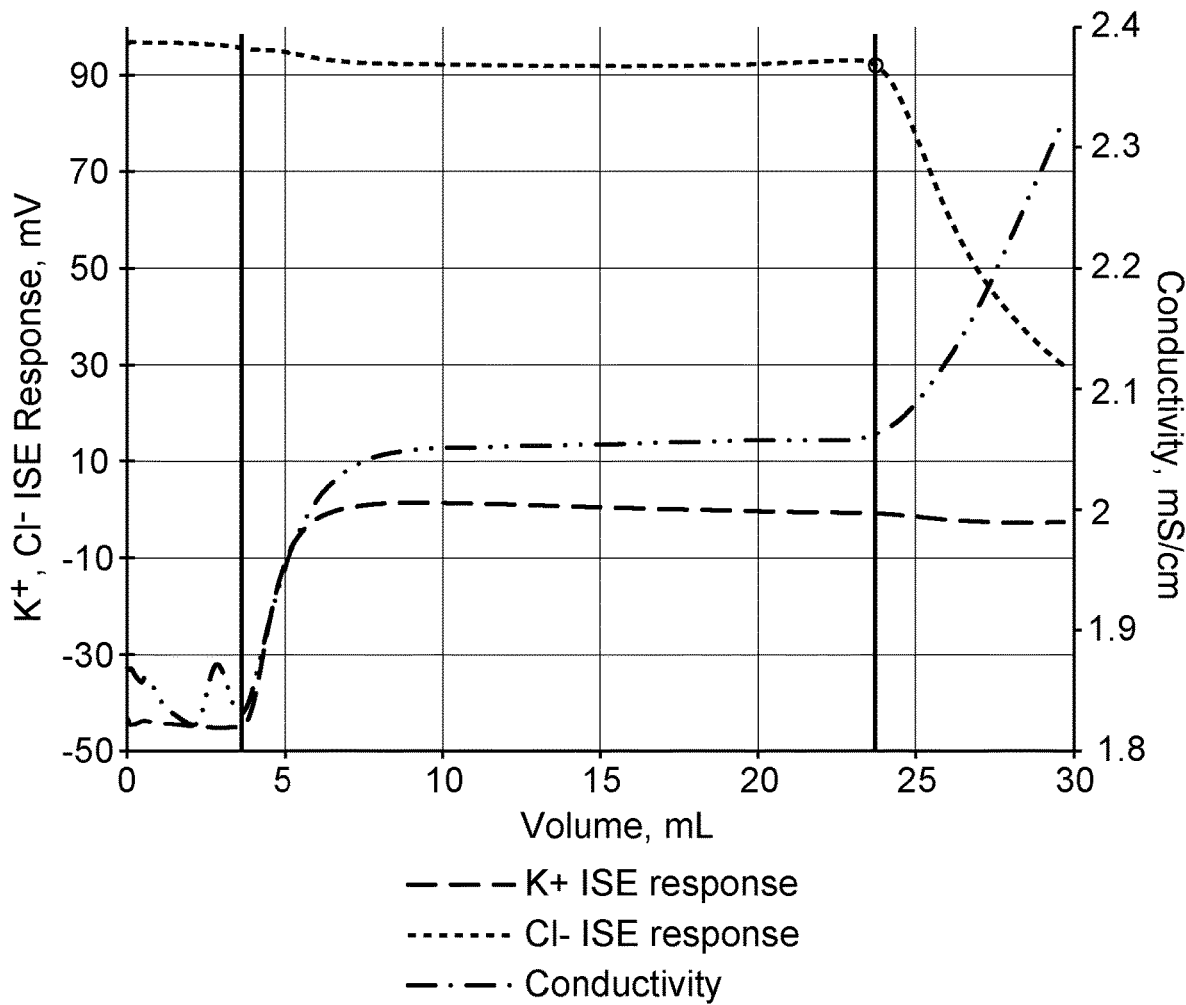
FIG. 6 is the chromatogram of Example 6 showing the concentration of potassium ion and chloride ion versus elution volume for a cation exchange media using two ion selective electrodes and a conductivity detector.

Potassium and chloride ISE responses, as well as UV absorption, versus challenge volume are shown in FIG. 5. Potassium and chloride ISE responses, as well as conductivity, versus challenge volume are shown in FIG. 6.

Inflections in the potassium and chloride ISE signals indicated the breakthrough of nonbinding potassium ions and binding chloride ions, respectively. A breakthrough criterion for each ISE signal was established, such that the challenge volume at which the ISE response departed by 1% from the average baseline response value prior to the inflection was defined as the breakthrough volume (BV) for the corresponding ion. The K⁺ breakthrough volume was then subtracted from the Cl⁻ breakthrough volume to obtain the net breakthrough volume (NBV). The known KCl concentration of the challenge solution (20 mM) and the frontal surface area of the anion exchange capsule (3.2 cm²) were then used to calculate the chloride dynamic binding capacity (DBC) of the capsule in equivalents of chloride per liter of unit area, according to Equation 4:

$$\text{Capacity }[microeq/cm^2] = \frac{\text{Net breakthrough volume [mL]}}{3.2 \text{ cm}^2} \times \frac{1 \text{ L}}{1000 \text{ mL}} \times \frac{\frac{20}{1000} eq}{1 \text{ L}} \times \frac{1{,}000{,}000 \text{ microeq}}{1 \text{ eq}} \quad \text{(Equation 4)}$$

As shown by the vertical line in FIG. 5, the breakthrough of chloride, as measured by the chloride ISE, was coincident with the onset of a monotonic increase in the UV absorption, indicating that a UV detector could be used instead of an ISE to detect chloride breakthrough.

As shown by the two vertical lines in FIG. 6, the breakthrough events for both potassium and chloride were coincident with the onset of increases in the outlet fluid conductivity, indicating that a conductivity probe could be used instead of an ISE to detect either or both of the potassium and chloride breakthrough events.

Example 7

Example 7 demonstrates that the methods of the present application may be used to determine viral clearance capacity.

Five anion exchange devices were obtained (each comprising a stack of 4 FNW and 3 downstream GFM membranes and having a frontal surface area of 3.2 cm²) and are hereinafter referred to as Capsule A, Capsule B, Capsule C, Capsule D and Capsule E. Capsules A-D were purposefully damaged by creating a hole through the entire stack using different sizes of blunt-tip syringe needles with, respectively, diameters of 0.5 mm, 0.9 mm, 1.2 mm and 1.4, following the procedure previously described in Examples 3-4. Capsule E remained intact.

A tangential flow filtration system was obtained (PENDOTECH TFF) and used as a control and data logging system. The outlet of the Capsule was connected to the inlet of an ISE probe fixture assembly with mounted potassium and chloride ISE probes. An instrument control unit (PENDOTECH PENDOKIT) was used to measure the potassium and chloride ISE signal. The outlet of the ISE probe fixture assembly was connected to a mass balance to measure weight and volume.

Capsules A-E were initially flushed with 30 mL of First Solution A at a flow rate of 3 mL/min. During this equilibrium step, the outlet fluid from the anion exchange device was directed to waste. Next, Washing Solution was flowed through the Capsule (15 mL at 1.5 mL/min) to wash the device. During this wash step, outlet fluid from the Capsule was directed to waste. After the wash step, the outlet fluid from the Capsule was connected to the potassium and chloride ISEs via the ISE probe fixture assembly and Washing Solution was run through the Capsule and ISE probe fixture assembly for 6 mL at 1 mL/min. In the final step, the Capsule's integrity was assessed by running Challenge Solution at a flow rate of 1 mL/min for 45 minutes, while monitoring the potassium and chloride ISE signals. The K+ and Cl— breakthrough volumes were then determined, and the difference was measured to determine the net breakthrough volume. The known KCl concentration and Capsule frontal surface area were then used to calculate the chloride dynamic binding capacity of the capsule in equivalents of chloride per frontal area of the membrane device, as described in Equation 5.

$$\text{Capacity [meq/cm}^2\text{]} = \frac{\text{Net breakthrough volume [mL]}}{3.0 \text{ cm}^2} \times \frac{1 \text{ L}}{1000 \text{ mL}} \times \frac{\frac{20}{1000}eq}{1 \text{ L}} \times \frac{1,000,000 \text{ meq}}{1 \text{ eq}} \quad \text{(Equation 5)}$$

After determining chloride dynamic binding capacity of Capsules A-E, viral clearance capacity was measured. Stocks of bacteriophage Phi X174 at 0.5×10$^{10}$ PFU/mL and Phi X174 Challenge Solutions were prepared as described above. About 1 mL of the phage challenge solution was set aside as an unchallenged control condition.

To determine viral clearance capacity for each of the damaged (Capsules A-D) and control (Capsule E) conditions, 50 mM Tris buffer (pH 7.5) was flushed through the anion exchange devices at 1 mL/min for 4 mL. Phage challenge solutions were then flushed through the anion exchange device at the same flow rate and 10 mL aliquots were collected from the outlet of the device.

Post-clearance phage challenge solution aliquots from all damaged (Capsules A-D) and control (Capsule E) conditions at varying dilutions were plated on agar plates with *Escherichia coli* cultures at 37° C. for 3-4 hours until plaques became visible. Plaques were then counted and compared to the initial unchallenged condition to determine the clearance capability of the Capsule. Results are summarized in Table 7, below.

TABLE 7

| | Capsule A | Capsule B | Capsule C | Capsule D | Capsule E |
|---|---|---|---|---|---|
| Pre-damage K$^+$ BV (mL) | 8.6 | 7.7 | 7.3 | 7.8 | 7.4 |
| Pre-damage Cl$^-$ BV (mL) | 25.6 | 26.1 | 26.4 | 27.2 | 25.8 |
| Pre-damage NBV (mL) | 17 | 18.4 | 19.1 | 19.4 | 18.4 |
| Pre-damage Cl$^-$ DBC (equiv/L) | 135 | 147 | 153 | 155 | 147 |
| Post-damage K$^+$ BV (mL) | 8.1 | 8.3 | 7.0 | 7.6 | n/a |
| Post-damage Cl$^-$ BV (mL) | 25.4 | 23.1 | 17.5 | 20.3 | n/a |
| Post-damage NBV (mL) | 17.3 | 14.8 | 10.5 | 12.7 | n/a |
| Post-damage Cl$^-$ DBC (meq/cm$^2$) | 129 | 127 | 84 | 102 | n/a |
| Change in BV (mL) | −0.3 | 3.6 | 8.6 | 6.7 | n/a |
| Viral Clearance (LRV) | 3.19 | 2.73 | 0.47 | TNTC | 3.76 |

TNTC: Too numerous to count
n/a: not applicable

Example 8

Example 8 is similar to Example 7, except that (1) the frontal area of the anion exchange device was 1 cm$^2$; and (2) the blunted syringe needles used to damage Capsules F-H layers had, respectively, diameters of 0.5 mm, 0.7 mm, and 1.2 mm.

Four anion exchange capsules were obtained, each comprising a stack of 4 FNW and 3 downstream GFM membranes). Capsules F-H were damaged as described above. Capsule 1 remained intact and was used as a control.

Capsules F-I were initially flushed with 10 mL of First Solution A at a flow rate of 1 mL/min. During this equilibrium step, the outlet fluid from the anion exchange device was directed to waste. Next, Washing Solution was run through the Capsule (4 mL at 1.5 mL/min) to wash the device. During this wash step, outlet fluid from the Capsule was directed to waste. After the wash step, the outlet fluid from the Capsule was connected to the potassium and chloride ISEs via the ISE probe fixture assembly and Washing Solution was run through Capsule and ISE probe fixture assembly for 4 mL at 1 mL/min. In the final step, the Capsule integrity was then assessed by using Challenge Solution at a flow rate of 1 mL/min, while monitoring the potassium and chloride ISE signals. The K+ and Cl— breakthrough volumes were then determined, and the difference was measured to determine the net breakthrough volume. The known KCl concentration and Capsule frontal surface area were then used to calculate the chloride dynamic binding capacity of the capsule in equivalents of chloride per frontal area of the membrane device, as described in Equation 6.

Equation 6

$$\text{Capacity [meq/cm}^2\text{]} = \frac{\text{Net breakthrough volume [mL]}}{1.0 \text{ cm}^2} \times \frac{1 \text{ L}}{1000 \text{ mL}} \times \frac{\frac{20}{1000}eq}{1 \text{ L}} \times \frac{1,000,000 \text{ meq}}{1 \text{ eq}} \quad \text{(Equation 6)}$$

After determining chloride dynamic binding capacity of Capsules F-I, viral clearance capacity was measured following the procedure described in Example 7. Results are summarized in Table 9, below.

TABLE 9

|  | Capsule F | Capsule G | Capsule H | Capsule I |
|---|---|---|---|---|
| Pre-damage K$^+$ BV (mL) | 7.1 | 7.3 | 6.6 | 7.4 |
| Pre-damage Cl$^-$ BV (mL) | 14.3 | 14.3 | 13.4 | 15.1 |
| Pre-damage NBV (mL) | 7.2 | 7.0 | 6.8 | 7.7 |
| Pre-damage Cl$^-$ DBC (meq/cm$^2$) | 144 | 140 | 136 | 154 |
| Post-damage K$^+$ BV (mL) | 7.1 | 7.5 | 7.2 | n/a |
| Post-damage Cl$^-$ BV (mL) | 12.8 | 12.3 | 12.7 | n/a |
| Post-damage NBV (mL) | 5.7 | 4.8 | 5.5 | n/a |
| Post-damage Cl$^-$ DBC (meq/cm$^2$) | 114 | 96 | 110 | n/a |
| Change in BV (mL) | 1.5 | 2.2 | 1.3 | n/a |
| Viral Clearance (LRV) | 3.09 | 2.04 | 1.96 | 4.4 | n/a: not applicable

Foreseeable modifications and alterations of this invention will be apparent to those skilled in the art without departing from the scope and spirit of this invention. This invention should not be restricted to the embodiments that are set forth in this application for illustrative purposes. To the extent that there is any conflict or discrepancy between this specification as written and the disclosure in any document mentioned or incorporated by reference herein, this specification as written will prevail.

What is claimed is:

1. A method for testing a chromatography device, said chromatography device having an inlet and an outlet and containing an ion exchange media, the method comprising:
   (a) providing the ion exchange media having a first ion bound to the ion exchange sites of the ion exchange media;
   (b) contacting the ion exchange media with a challenge solution, wherein the challenge solution comprises (i) a second ion, which binds to the ion exchange media and (ii) a non-binding species, which does not bind to the ion exchange media, wherein the second ion has a higher binding affinity to the ion exchange media than the first ion;
   (c) monitoring an outlet fluid from the outlet of the chromatography device with at least one detector wherein both the second ion and the non-binding species are monitored;
   (d) recording a breakthrough value of (i) the second ion and (ii) the non-binding species; and
   (e) calculating a net breakthrough value using the breakthrough value of the non-binding species and the breakthrough value of the second ion.

2. The method of claim 1 comprising contacting the ion exchange media with a first solution comprising the first ion prior to contacting the ion exchange media with the challenge solution, optionally further comprising washing the chromatography device with a dilute solution after contacting the ion exchange media with the first solution, wherein the dilute solution contains neither the second ion nor the non-binding ion.

3. The method of claim 2, wherein the dilute solution is water or a dilute salt solution.

4. The method of claim 3, wherein the concentration of the first ion is lower in said dilute salt solution than in the first solution.

5. The method of claim 1, wherein the first ion is acetate.

6. The method of claim 1, wherein the second ion is chloride.

7. The method of claim 1, wherein the non-binding species is potassium ion.

8. The method of claim 1, wherein the first ion is lithium, and optionally wherein the non-binding species is a chloride ion.

9. The method of claim 8, wherein the second ion is potassium.

10. The method of claim 1, wherein the ion exchange media comprises at least one of a membrane, a functionalized nonwoven, a monolith, and a packed bed.

11. The method of claim 1, wherein the at least one detector is selected from at least one of UV, conductivity, ion selective electrode, mass spectrometry, fluorescence, and luminescence.

12. The method of claim 1, wherein the outlet fluid is monitored with at least two detectors and optionally, wherein at least one of the at least two detectors is an ion selective electrode.

13. The method of claim 1, further comprising comparing the net breakthrough value to a known value of a reference integral device to determine integrity of the chromatography device.

14. The method of claim 1, further comprising determining the adsorbent capacity from the net breakthrough value and comparing the adsorbent capacity with an expected adsorbent capacity.

15. The method of claim 1, wherein the net breakthrough value is used to predict an expectant level of viral clearance.

16. The method of claim 1, further comprising: passing a product-containing fluid through the chromatography device after monitoring the outlet fluid for the second ion and the non-binding species.

17. The method of claim 16, further comprising performing a gas pressure-based integrity test after passing a product-containing fluid through the chromatography device, and optionally wherein the gas pressure-based integrity test is selected from ASTM F316-03 (2011) or ASTM D 6908-06 (2017).

* * * * *